United States Patent [19]

Trainor et al.

[11] Patent Number: 4,880,780

[45] Date of Patent: Nov. 14, 1989

[54] SELECTED DIFLUORO DERIVATIVES

[75] Inventors: Diane A. Trainor, Glen Mills, Pa.; Mark M. Stein, Wilmington, Del.

[73] Assignee: ICI Americas Inc., Wilmington, Del.

[21] Appl. No.: 58,079

[22] Filed: Jun. 4, 1987

Related U.S. Application Data

[63] Continuation-in-part of Ser. No. 872,106, Jun. 6, 1986, abandoned.

[30] Foreign Application Priority Data

Jun. 7, 1985 [GB] United Kingdom ............... 8514436
Jun. 7, 1985 [GB] United Kingdom ............... 8514438
Jun. 7, 1985 [GB] United Kingdom ............... 8514440

[51] Int. Cl.$^4$ .................. A61K 37/43; C07K 5/08
[52] U.S. Cl. ................................. 514/18; 530/331
[58] Field of Search ......................... 514/18; 530/331

[56] References Cited

U.S. PATENT DOCUMENTS 4,277,395 7/1981 Bey et al. ......................... 530/330

FOREIGN PATENT DOCUMENTS 0130679 1/1985 European Pat. Off. .

845183 7/1984 South Africa .

OTHER PUBLICATIONS

Gelb, Michael H., et al., *Biochemistry* (1985) 24 (8), 1813.

*Primary Examiner*—Delbert R. Phillips
*Attorney, Agent, or Firm*—Rosemary M. Miano; Thomas E. Jackson

[57] ABSTRACT

The invention discloses a series of difluoroketone, mono- di- and tri-peptide derivatives of formula Ia, Ib and Ic:

| | |
|---|---|
| (Formula set out on pages following Examples) | Ia |
| (Formula set out on pages following Examples) | Ib |
| (Formula set out on pages following Examples) | Ic | and salts thereof where appropriate, and wherein the radicals are defined hereafter in the specification. The derivatives are useful in inhibiting the action of human leukocyte elastase. There are also disclosed methods and intermediates for the manufacture of, and pharmaceutical compositions comprising, the said derivatives.

9 Claims, No Drawings

SELECTED DIFLUORO DERIVATIVES

This application is a continuation-in-part of U.S. Ser. No. 872,106, filed June 6, 1986, and now abandoned.

BACKGROUND AND SUMMARY OF THE INVENTION

The present invention relates to certain difluoro ketone peptide derivatives which are human leukocyte elastase (HLE) inhibitors and are also useful as research tools in pharmacological and related studies and in the treatment of tissue degenerative diseases such as pulmonary emphysema, atherosclerosis, rheumatoid arthritis and osteoarthritis in warm blooded animals. The invention also includes intermediates useful in the synthesis of these peptide derivatives, processes for preparing them, pharmaceutical compositions containing such peptide derivatives and methods for their use. Proline based peptide aldehydes are disclosed in European Patent Application 84302621.2. Fluoroketone inhibitors of hydrolytic enzymes are disclosed in Gelb, M. H. et al, *Biochemistry* (1985) 24, 1813–1817 for non-serine proteases. Imperiali, B. et al, *Tetra. Letters* (1986) 27, No. 2, 135–138 shows selected fluoromethyl ketones. Thaisrivongs, S. et al, *J. Med. Chem.* (1985) 28, No. 11, 1553–1555 discloses selected fluoro ketones as renin inhibitors.

DESCRIPTION OF THE INVENTION

The substituted peptides of the present invention may be represented by the following formulae Ia, Ib and Ic:

| (Formula set out on pages following Examples) | Ia |
| (Formula set out on pages following Examples) | Ib |
| (Formula set out on pages following Examples) | Ic | wherein
$R^1$ is alkyl;
$R^2$ is alkyl, substituted alkyl, aryl, substituted aryl, aralkyl or substituted aralkyl;
$R^3$ is alkyl, substituted alkyl, cycloalkyl, substituted cycloalkyl, alkenyl, substituted alkenyl, aryl, substituted aryl, aralkyl, substituted aralkyl, an aliphatic heterocycle, a substituted aliphatic heterocycle, an aromatic heterocycle or a substituted aromatic heterocycle;
$R^4$ is hydrogen or methyl;
$R^A$ is represented by the following formula II:

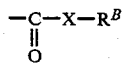   II or is $CH_3$, $CH_2R^B$, or $CHR^B R^D$
wherein $R^B$ is alkyl, aralkyl, cycloalkyl, cycloalkylalkyl or aryl, wherein the aryl group or the aryl portion of the aralkyl may optionally bear 1 to 3 substituents;
X is $CH_2$, $CHR^D$ or $NR^C$ with $R^C$ being hydrogen or $CH_3$;
$R^D$ is alkyl or arylalkyl;
A is selected from the group consisting of

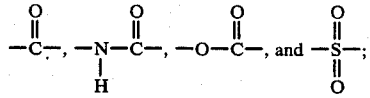

and pharmaceutically acceptable salts thereof.

Particular compounds are those wherein
$R^1$ is an alkyl group containing from 1 to 5 carbon atoms, and more preferably from 2 to 5 carbon atoms;
$R^2$ is selected from the group consisting of:
 (I) an alkyl group containing from 1 to 10 carbons;
 (II) an alkyl group containing from 1 to 6 carbon atoms substituted by at least one member selected from the group consisting of:
  (a) hydroxy;
  (b) amino;
  (c) alkylamino containing from 1 to 6 carbons;
  (d) dialkylamino wherein each alkyl group contains from 1 to 6 carbons;
  (e) alkanoyl containing from 2 to 6 carbons;
  (f) arylcarbonyl wherein the aryl contains 6, 10 or 12 carbons;
  (g) aralkanoyl containing 8 to 13 carbons;
  (h) amido which may be attached to the alkyl group via either a nitrogen or carbon of said amido;
  (i) alkylcarbonylamino wherein the alkyl group contains from 1 to 6 carbons;
  (j) alkylaminocarbonyl wherein the alkyl group contains from 1 to 6 carbons;
  (k) arylcarbonylamino wherein the aryl group contains 6, 10 or 12 carbons;
  (l) aralkylcarbonylamino wherein the aralkyl group contains from 7 to 13 carbons;
  (m) arylaminocarbonyl wherein the aryl group contains 6, 10 or 12 carbons;
  (n) aralkylaminocarbonyl wherein the aralkyl group contains from 7 to 13 carbons;
  (o) carboxy;
  (p) aryloxycarbonyl wherein the aryl group contains 6, 10 or 12 carbons;
  (q) aralkoxycarbonyl wherein the aralkoxy group contains from 7 to 13 carbons;
  (r) alkanoyloxy containing from 2 to 6 carbons;
  (s) aroyloxy wherein the aryl portion contains 6, 10 or 12 carbons;
  (t) aralkanoyloxy containing from 8 to 14 carbons;
  (u) alkylsulfonamideo wherein the alkyl group contains from 1 to 6 carbons;
  (v) aralkylsulfonamido wherein the aralkyl group contains from 7 to 13 carbons;
  (w) arylsulfonamido wherein the aryl group contains 6, 10 or 12 carbons;
  (x) acylsulfonamideo (i.e., acylaminosulfonyl and sulfonylaminocarbonyl) (2 to 15 carbons) including acylsulfonamido wherein the acyl group contains 1 to 7 carbons when it is the terminal portion of the acylsulfonamide and provided that when the acylsulfonamido contains an aryl the aryl contains 6, 10 or 12 carbons and may be further substituted by a member selected from fluoro, chloro, bromo, iodo and nitro;

(y) alkoxycarbonyl wherein the alkoxy group contains from 1 to 6 carbons;
(z) aralkoxycarbonylamino containing from 8 to 13 carbons (e.g., benzyloxycarbonylamino);
(aa) aryloxycarbonylamino wherein the aryloxy group contains 6, 10 or 12 carbons;
(bb) alkoxycarbonylamino wherein the alkyloxy group contains from 1 to 6 carbons;
(cc) aryl containing 6, 10 or 12 carbons (e.g., phenyl, biphenyl, naphthyl);
(dd) aryl containing 6, 10 or 12 carbons and substituted by 1 to 3 members selected from the group consisting of chloro, bromo, iodo, fluoro, trifluoromethyl, hydroxy, alkyl (1 to 6 carbons), alkoxy (1 to 6 carbons), alkylcarbonyloxy (2 to 6 carbons), alkoxycarbonyl (1 to 6 carbons), carboxy, 5-tetrazolo, and acylsulfonamido (i.e. acylaminosulfonyl and sulfonylaminocarbonyl) (2 to 15 carbons) and provided that when the acylsulfonamido contains an aryl the aryl contains 6, 10 or 12 carbons and may be further substituted by a member selected from fluoro, chloro, bromo, iodo and nitro;
(ee) cycloalkyl containing from 3 to 15 carbons (e.g., cyclohexyl, adamantyl, norbornyl);
(ff) alkylureido wherein the alkyl group contains from 1 to 6 carbons;
(gg) aralkylureido containing from 8 to 13 carbons;
(hh) arylureido wherein the aryl group contains 6, 10 or 12 carbons; and
(III) an aryl group of 6 carbons, e.g. phenyl;
$R^3$ is selected from the group consisting of:
(I) an alkyl group containing from 1 to 12 carbons;
(II) an alkyl group containing from 1 to 12 carbons and from 1 to 4 hetero atoms each of which is selected independently from the group consisting of nitrogen and oxygen;
(III) an alkyl group containing from 1 to 12 carbons and, optionally, 1 to 4 hetero atoms each of which is selected independently from the group consisting of nitrogen and oxygen, and substituted on at least one of carbon or nitrogen by 1 to 3 members selected independently from the group consisting of:
For carbon:
(a) hydroxy, provided that it may not be on a carbon directly bonded to A;
(b) amino, provided that it may not be on a carbon directly bonded to A;
(c) alkylamino containing from 1 to 6 carbons, provided that it may not be on a carbon directly bonded to A;
(d) dialkylamino wherein each alkyl group contains from 1 to 6 carbons, provided that it may not be on a carbon directly bonded to A;
(e) alkanoyl containing from 2 to 6 carbons;
(f) arylcarbonyl wherein the aryl contains 6, 10 or 12 carbons;
(g) aralkanoyl containing 8 to 13 carbons;
(h) amido which may be attached to the alkyl group via either a nitrogen or carbon of said amido;
(i) alkylcarbonylamino wherein the alkyl group contains from 1 to 6 carbons;
(j) alkylaminocarbonyl wherein the alkyl group contains from 1 to 6 carbons;
(k) arylcarbonylaminio wherein the aryl group contains 6, 10 or 12 carbons;
(k)-(1) arylcarbonylamino wherein the aryl group contains 6, 10 or 12 carbons and is substituted by a member selected from carboxy, alkoxycarbonyl, where alkoxy is 1 to 3 carbons, 5-tetrazolo, and acylsulfonamido (i.e., acylaminosulfonyl and sulfonylaminocarbonyl) containing 2 to 15 carbons and provided that when the acylsulfonamido contains an aryl the aryl contains 6, 10 or 12 carbons and may be further substituted by a member selected from fluoro, chloro, bromo, iodo and nitro;
(l) aralkylcarbonylamino wherein the aralkyl group contains from 7to 13 carbons;
(l)-(1) aralkylcarbonylamino wherein the aralkyl group contains 7 to 13 carbons and is substituted on the aryl portion by a member selected from carboxy, alkoxycarbonyl, where the alkoxy has 1 to 3 carbons, 5-tetrazolo, and acylsulfonamido (i.e., acylaminosulfonyl and sulfonylaminocarbonyl) containing 2 to 15 carbons and provided that when the acylsulfonamido contains an aryl the aryl contains 6, 10 or 12 carbons and may be further substituted by a member selected from fluoro, chloro, bromo, iodo and nitro;
(m) arylaminocarbonyl wherein the aryl group contains 6, 10 or 12 carbons;
(n) aralkylaminocarbonyl wherein the aralkyl group contains from 7 to 13 carbons;
(o) carboxy;
(p) aryloxycarbonyl wherein the aryl group contains 6, 10 or 12 carbons;
(q) aralkoxycarbonyl wherein the aralkoxy group contains from 7 to 13 carbons;
(r) alkanoyloxy containing from 2 to 6 carbons;
(s) aroyloxy wherein the aryl portion contains 6, 10 or 12 carbons;
(t) aralkanoyloxy containing from 8 to 13 carbons;
(u) alkylsulfonamido wherein the alkyl group contains from 1 to 6 carbons;
(u)-(1) cycloalkylsulfonamido wherein the cycloalkyl portion contains 3 to 15 carbons (e.g., cyclohexyl, adamantyl, norbornyl);
(v) aralkylsulfonamido wherein the aralkyl group contains from 7 to 13 carbons;
(w) arylsulfonamido wherein the aryl group contains 6, 10 or 12 carbons;
(x) acylsulfonamido (i.e., acylaminosulfonyl and sulfonylaminocarbonyl) (2 to 15 carbons) including acylsulfonamido wherein the acyl group contains 1 to 7 carbons when it is the terminal portion of the acylsulfonamide, and provided that when the acylsulfonamido contains an aryl the aryl contains 6, 10 or 12 carbons and may be further substituted by a member selected from fluoro, chloro, bromo, iodo and nitro;
(y) alkoxycarbonyl wherein the alkoxy group contains from 1 to 6 carbons;
(z) aralkoxycarbonylamino containing from 8 to 13 carbons (e.g., benzyloxycarbonylamino);
(z)-(1) aralkylaminocarbonyloxy containing 8 to 13 carbons;

(z)-(2) aryloxy wherein the aryl contains 6, 10 or 12 carbons;

(z)-(3) aryloxy wherein the aryl contains 6, 10 or 12 carbons and is substituted by a member selected from aminocarbonyl, aminocarbonylalkyl where the alkyl has 1 to 3 carbons, alkoxycarbonyl having 1 to 3 carbons, and carboxy;

(aa) aryloxycarbonylamino wherein the aryloxy group contains 6, 10 or 12 carbons;

(aa)-(1) arylaminocarbonyloxy wherein the aryl group contains 6, 10 or 12 carbons;

(bb) alkoxycarbonylamino wherein the alkyloxy group contains from 1 to 6 carbons;

(bb)-(1) alkoxycarbonylamino wherein the alkoxy group contains 1 to 6 carbons and is optionally bonded on carbon to a carbon of an aromatic heterocyclic group as described in (gg) under $R^3$;

(bb)-(2) alkoxycarbonylamino wherein the alkoxy group contains 1 to 6 carbons substituted by an aliphatic heterocyclic group as described in (ff) under $R^3$;

(bb)-(3) aryloxyalkylcarbonylamino wherein the aryl contains 6 L or 10 carbons and the alkyl has 1 to 6 carbons;

(bb)-(4) alkylaminocarbonyloxy wherein the alkyl group contains 1 to 6 carbons;

(cc) aryl containing 6, 10 or 12 carbons (e.g., phenyl, naphthyl, biphenyl);

(cc)-(1) aryloxy containing 6, 10 or 12 carbons;

(dd) aryl containing 6, 10 or 12 carbons and substituted by 1 to 3 members independently selected from the group consisting of chloro, bromo, iodo, fluoro, hydroxy, trifluoromethyl, alkyl (1 to 6 carbons), alkoxy (1 to 6 carbons), alkanoyloxy (2 to 6 carbons), alkoxycarbonyl (2 to 6 carbons), carboxy, aminocarbonylalkyl (2 to 6 carbons), aminocarbonyl, 5-tetrazolo, and acylsulfonamido (i.e., acylaminosulfonyl and sulfonylaminocarbonyl) (2 to 15 carbons), and provided that when the acylsulfonamido contains an aryl the aryl contains 6, 10 or 12 carbons and may be further substituted by a member selected from fluoro, chloro, bromo, iodo and nitro;

(dd)-(1) aryloxy containing 6, 10 or 12 carbons and substituted on carbon by 1 to 3 members independently selected from the group consisting of chloro, bromo, iodo, fluoro, hydroxy, trifluoromethyl, alkyl (1 to 6 carbons), alkoxy (1 to 6 carbons), alkanoyloxy (2 to 6 carbons), alkoxycarbonyl (2 to 6 carbons), carboxy, aminocarbonylalkyl (2 to 6 carbons), aminocarbonyl, 5-tetrazolo, acylsulfonamido (i.e., acylaminosulfonyland sulfonylaminocarbonyl) (2 to 15 carbons) and provided that when the acylsulfonamido contains an aryl the aryl contains 6, 10 or 12 carbons and may be further substituted by a member selected from fluoro, chloro, bromo, iodo and nitro;

(ee) cycloalkyl containing from 3 to 15 carbons (e.g., cyclohexyl, adamantyl, norbornyl);

(ee)-(1) cycloalkyloxy containing from 3 to 15 carbons;

(ff) an aliphatic heterocyclic group of at least 4 atoms containing from 1 to 5 carbons and from 1 to 4 hetero atoms each of which is selected independently from the group consisting of hydrogen and oxygen (e.g., morpholine, piperazine), wherein the aliphatic heterocyclic group may optionally contain 1 or 2 double bond(s), which aliphatic heterocyclic group may be substituted at any nitrogen with an alkyl group containing from 1 to 6 carbons, an alkanoyl group containing from 1 to 6 carbons, an aryloxycarbonyl group wherein the aryl group contains 6, 10 or 12 carbon atoms, an aralkyloxycarbonyl group wherein the aralkyl group contains from 7 to 13 carbons or an alkoxycarbonyl group wherein the alkyl group contains from 1 to 6 carbons;

(ff)-(1) an aliphatic heterocyclic oxy group wherein the oxy link is bonded directly to a carbon atom of the aliphatic heterocyclic group of at least 5 atoms containing from 1 to 5 carbons and from 1 to 4 hetero atoms each of which is selected independently from the group consisting of nitrogen and oxygen, (e.g., morpholine, piperazine), wherein the aliphatic heterocyclic group may optionally contain 1 or 2 double bond(s), which aliphatic heterocyclic group may be substituted at any nitrogen with an alkyl group containing from 1 to 6 carbons, an alkanoyl group containing from 1 to 6 carbons, an aryloxycarbonyl group wherein the aryl group contains 6, 10 or 12 carbons, an aralkyloxycarbonyl group wherein the aralkyl group contains from 7 to 13 carbons or an alkoxycarbonyl group wherein the alkyl group contains from 1 to 6 carbons;

(gg) an aromatic heterocyclic group of from 1 to 15 carbons and from 1 to 4 heteroatoms each of which is selected independently from the group consisting of sulfur, nitrogen and oxygen and which form 1 to 3 five or six-membered rings at least one of which is aromatic, and optionally, wherein up to 3 carbons of the aromatic ring(s) may be substituted with a member of the group consisting of fluoro, chloro, bromo, iodo, trifluoromethyl, alkyl containing from 1 to 6 carbons, alkoxy containing from 1 to 6 carbons, alkanoyl containing from 2 to 6 carbons, carboxy, aminocarbonylalkyl (2 to 6 carbons) and aminocarbonyl, and provided further that any nitrogen atom may be substituted by an alkyl group containing from 1 to 6 carbon atoms;

(gg)-(1) an aromatic heterocyclic oxy group wherein the oxy link is bonded directly to a carbon of an aromatic heterocyclic group of from 1 to 15 carbons and from 1 to 4 heteroatoms each of which is selected independently from the group consisting of sulfur, nitrogen and oxygen and which form 1 to 3 five or six-membered rings at least one of which is aromatic, and optionally, wherein up to 3 carbons of the aromatic ring(s) may be substituted with a member of the group consisting of fluoro, chloro, bromo, iodo, trifluoromethyl, alkyl containing from 1 to 6 carbons, alkoxy containing from 1 to 6 carbons, alkanoyl containing from 2 to 6 carbons, carboxy, aminocarbonylalkyl (2 to 6 carbons) and aminocarbonyl, and provided further that any nitrogen atom may be substituted by an alkyl group containing from 1 to 6 carbons;
(hh) alkylureido wherein the alkyl group contains from 1 to 6 carbon atoms;
(hh)-(1) cycloalkylureido wherein the cycloalkyl group contains 3 to 15 carbons;
(ii) aralkylureido wherein the aralkyl group contains from 7 to 13 carbons;
(jj) arylureido wherein the aryl group contains 6, 10 or 12 carbons;
(jj)-(1) arylureido wherein the aryl group contains 6, 10 or 12 carbons and is substituted by 1 to 3 members selected independently from the group consisting of chloro, bromo, iodo, fluoro, hydroxy, trifluoromethyl, alkyl (1 to 6 carbons), alkoxy (1 to 6 carbons), alkanoyloxy (2 to 6 carbons), alkoxycarbonyl (2 to 6 carbons), carboxy, aminocarbonylalkyl (2 to 6 carbons), aminocarbonyl, 5-tetrazolo, and acylsulfonamido (i.e., acylaminosulfonyl and sulfonylaminocarbonyl) (2 to 15 carbons) including acylsulfonamido wherein the acyl group contains 1 to 7 carbons when it is the terminal portion of the acylsulfonamide and provided that when the acylsulfonamido contains an aryl the aryl contains 6, 10 or 12 carbons and may be further substituted by a member selected from fluoro, chloro, bromo, iodo and nitro;

For nitrogen:
(a) alkyl of 1 to 3 carbons;
(b) alkanoyl containing from 2 to 6 carbon atoms;
(c) arylcarbonyl wherein the aryl contains 6, 10 or 12 carbons;
(d) aralkanoyl containing 8 to 14 carbons;
(e) formyl;
(f) an aliphatic heterocyclic group as defined in (ff) for the carbon substituents wherein the nitrogen is bonded directly to a carbon of the aliphatic heterocyclic group;
(g) an aromatic heterocyclic group as defined in (gg) for the carbon substituents wherein the nitrogen is bonded directly to a carbon of the aromatic heterocyclic group;

(IV) an aryl group containing 6, 10 or 12 carbons;
(V) an aryl group containing 6, 10 or 12 carbons suitably substituted by 1 to 3 members selected independently from the group consisting of fluoro, chloro, bromo, iodo, trifluoromethyl, hydroxy, alkyl containing from 1 to 6 carbons, alkanoyloxy (2 to 6 carbons), alkoxy containing from 1 to 6 carbons, alkoxycarbonyl containing from 2 to 6 carbons, carboxy, alkylcarbonylamino wherein the alkyl group contains 1 to 6 carbons, 5-tetrazolo, and acylsulfonamido (i.e., acylaminosulfonyl and sulfonylaminocarbonyl) containing from 2 to 15 carbons, and provided that when the acylsulfonamido contains an aryl the aryl contains 6, 10 or 12 carbons and may be further substituted by a member selected from fluoro, chloro, bromo, iodo and nitro;
(VI) a cycloalkyl group containing from 3 to 15 carbons (e.g., cyclohexyl, adamantyl, norbornyl);
(VI)-(1) a cycloalkyl group containing from 3 to 15 carbons (e.g., cyclohexyl, adamantyl, norbornyl), substituted by a member selected from the group consisting of carboxy, alkoxycarbonyl wherein the alkoxy group contains 1 to 4 carbons, 5-tetrazolo, and acylsulfonamido (i.e., acylaminosulfonyl and sulfonylaminocarbonyl) (2 to 15 carbons) including acylsulfonamido wherein the acyl group contains 1 to 7 carbons when it is the terminal portion of the acylsulfonamide and provided that when the acylsulfonamido contains an aryl the aryl contains 6, 10 or 12 carbons and may be further substituted by a member selected from fluoro, chloro, bromo, iodo and nitro;
(VII) an aliphatic heterocyclic group of at least 5 atoms containing from 1 to 5 carbons and from 1 to 4 hetero atoms each of which is selected independently from the group consisting of nitrogen and oxygen, (e.g., morpholine, piperazine) which may be substituted at any nitrogen with a member selected from the group consisting of an alkyl group containing from 1 to 6 carbon atoms, an alkanoyl group containing from 1 to 6 carbons, an aryloxycarbonyl group wherein the aryl group contains 6, 10 or 12 carbons, an aralkoxycarbonyl group wherein the aralkyl group contains from 7 to 13 carbons and an alkoxycarbonyl group containing from 2 to 7 carbons, provided that when A is OCO or NHCO then A must be bonded to a carbon atom of the aliphatic heterocyclic group;
(VIII) an aromatic heterocyclic group of from 1 to 15 carbons and from 1 to 4 heteroatoms each of which is selected independently from the group consisting of sulfur, nitrogen and oxygen, and which form 1 to 3 five or six-membered rings at least one of which is aromatic, and optionally, wherein up to 3 carbons of the aromatic ring(s) may be substituted at any carbon atom with a member of the group consisting of fluoro, chloro, bromo, iodo, trifluoromethyl, alkyl containing from 1 to 6 carbons, alkoxy containing from 1 to 6 carbons, alkanoyl containing from 2 to 6 carbons, carboxy, and provided further that any nitrogen may be substituted by an alkyl group containing from 1 to 6 carbons, provided that when A is OCO or NHCO then A must be bonded to a carbon of the aromatic heterocycle;
(IX) an alkenyl group of 2 to 10 carbons, having at least one double bond; and
(X) an alkenyl group of 2 to 10 carbons, having at least one double bond and substituted by a member selected from the group consisting of
(a) aryl of 6 or 10 carbons;
(b) aryl of 6 or 10 carbons substituted by 1 to 3 members selected independently from the group consisting of chloro, bromo, iodo, fluoro, hydroxy, trifluoromethyl, alkyl (1 to 6 carbons), alkoxy (1 to 6 carbons), alkanoyloxy (2 to 6 carbons), alkoxycarbonyl (2 to 6 carbons), carboxy, 5-tetrazolo, and acylsulfonamido (i.e., acylaminosulfonyl and sulfonylaminocarbonyl) (2 to 15 carbons) and provided that when the acylsulfonamido contains an aryl the aryl contains 6, 10 or 12 carbons and may be further substituted by a member selected from fluoro, chloro, bromo, iodo and nitro; and
(c) ureidocarbonyl;

$R^4$ is selected from the group consisting of hydrogen and methyl;

A is selected from the group consisting of

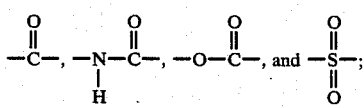

$R^A$ is selected from a group consisting of $CH_3$, $CH_2R^B$, $CHR^BR^D$ and a group of formula II wherein X is $CH_2$, $CHR^D$ or $NR^C$ as defined above;

$R^B$ is selected from the group consisting of (1–10C)alkyl, (5–15C)cycloalkyl, (5–15C)cycloalkyl-(1-6-C)alkyl (for example, adamantylmethyl), aryl having 6 or 10 carbons, and (6 or 10C)aryl(1–6C)alkyl, wherein any of the aryl portions may optionally be substituted with from 1 to 3 members independently selected from the group consisting of chloro, bromo, iodo, fluoro, trifluoromethyl, hydroxy, alkyl (1 to 6 carbons), alkoxy (1 to 6 carbons), alkoxycarbonyl (1 to 6 carbons), carboxy, 5-tetrazolo, and acylsulfonamido (i.e., acylaminosulfonyl and sulfonylaminocarbonyl) (2 to 15 carbons) and provided that when the acylsulfonamido contains an aryl the aryl may be further substituted by a member selected from fluoro, chloro, bromo, iodo and nitro;

$R^D$ is selected from the group consisting of (1–6C)alkyl and phenyl(1–6C)alkyl; and where appropriate, pharmaceutically acceptable salts thereof.

More particular values for compounds of the invention include the following members of the groups defined above:

$R^1$ is an alkyl group containing 3 carbons;

$R^2$ is selected from the group consisting of:
(I) an alkyl group containing from 1 to 4 carbons;
(II) an alkyl group containing from 1 to 4 carbons substituted by at least one member selected from the group consisting of:
  (e) alkanoyl containing from 2 to 3 carbons;
  (f) arylcarbonyl wherein the aryl contains 6 or 10 carbons (e.g., phenyl or naphthyl);
  (g) aralkanoyl containing 8 carbons (e.g., phenylacetyl);
  (h) amido which may be attached to the alkyl group via either a nitrogen or carbon of said amido;
  (i) alkylcarbonylamino wherein the alkyl group contains from 1 to 2 carbons;
  (j) alkylaminocarbonyl wherein the alkyl group contains from 1 to 2 carbons;
  (k) arylcarbonylamino wherein the aryl group contains 6 carbons (e.g., phenyl);
  (l) aralkylcarbonylamino wherein the aralkyl group contains 7 carbons;
  (m) arylaminocarbonyl wherein the aryl group contains 6 carbons;
  (n) aralkylaminocarbonyl wherein the aralkyl group contains 7 carbons;
  (o) carboxy;
  (p) aryloxycarbonyl wherein the aryl group contains 6 carbons;
  (q) aralkoxycarbonyl wherein the aralkoxy group contains 7 carbons;
  (r) alkanoyloxy containing from 1 to 2 carbons;
  (s) aroyloxy wherein the aryl portion contains 6 carbons;
  (t) aralkanoyloxy containing 8 carbons;
  (u) alkylsulfonamido wherein the alkyl group contains from 1 to 6 carbons;
  (v) aralkylsulfonamido wherein the aralkyl group contains from 7 to 13 carbons (e.g., 1-naphthylmethylsulfonylamino or 4-phenylbutylsulfonylamino);
  (w) arylsulfonamido wherein the aryl group contains 6 or 10 carbons;
  (x) acylsulfonamido containing 2 to 15 carbons (e.g., phenylsulfonylaminocarbonyl);
  (y) alkoxycarbonyl wherein the alkoxy group contains 1 or 2 carbons;
  (z) aralkoxycarbonylamino wherein the aralkoxy group contains 7 carbons (e.g., benzyloxycarbonylamino);
  (aa) aryloxycarbonylamino wherein the aryloxy group contains 6 carbons;
  (bb) alkoxycarbonylamino wherein the alkyloxy group contains from 1 to 3 carbons;
  (cc) aryl containing 6 or 10 carbons (e.g., phenyl or naphthyl);
  (dd) aryl containing 6 or 10 carbons and substituted by 1 to 3 members selected from the group consisting of chloro, bromo, iodo, fluoro, trifluoromethyl, hydroxy, alkyl (1 to 2 carbons), alkoxy (1 to 2 carbons), alkanoyloxy (2 to 6 carbons), alkoxycarbonyl (2 to 3 carbons), carboxy, 5-tetrazolo, and acylsufonamido (2 to 15 carbons);
  (ee) cycloalkyl containing from 3 to 15 carbons (e.g., cyclohexyl, adamantyl, norbornyl);
  (ff) alkylureido wherein the alkyl group contains from 1 to 2 carbons;
  (gg) aralkylureido wherein the aralkyl group contains 7 carbons;
  (hh) arylureido wherein the aryl group contains 6 or 10 carbons; and
(III) an aryl group of 6 carbons;

$R^3$ is selected from the group consisting of:
(I) an alkyl group containing from 1 to 12 carbons;
(II) an alkyl group containing from 1 to 12 carbons and from 1 to 4 hetero atoms each of which is selected independently from the group consisting of nitrogen and oxygen;
(III) an alkyl group containing from 1 to 12 carbons and, optionally, 1 to 4 hetero atoms each of which is selected independently from the group consisting of nitrogen and oxygen, and substituted on at least one of carbon or nitrogen by 1 to 3 members selected independently from the group consisting of:
For carbon:
  (e) alkanoyl containing from 2 to 6 carbons;
  (f) arylcarbonyl wherein the aryl contains 6, 10 or 12 carbons;
  (g) aralkanoyl containing 8 to 13 carbons;
  (h) amido which may be attached to the alkyl group via either a nitrogen or carbon of said amido;
  (i) alkylcarbonylamino wherein the alkyl group contains from 1 to 6 carbons;
  (j) alkylaminocarbonyl wherein the alkyl group contains from 1 to 6 carbons;
  (k) arylcarbonylamino wherein the aryl group contains 6 to 10 carbons;

(k)-(1) arylcarbonylamino wherein the aryl group contains 6 or 10 carbons and is substituted by a member selected from carboxy, alkoxycarbonyl, where alkoxy is 1 to 3 carbons, 5-tetrazolo, and acylsulfonamido containing 2 to 15 carbons;

(l) aralkylcarbonylamino wherein the aralkyl group contains from 7 to 13 carbons;

(l)-(1) aralkylcarbonylamino wherein the aralkyl group contains 7 to 13 carbons and is substituted by a member selected from carboxy, alkoxycarbonyl, where the alkoxy has 1 to 3 carbons, 5-tetrazolo, and acylsulfonamido containing 2 to 15 carbons;

(m) arylaminocarbonyl wherein the aryl group contains 6 or 10 carbons;

(n) aralkylaminocarbonyl wherein the aralkyl group contains from 7 to 13 carbons;

(o) carboxy;

(p) aryloxycarbonyl wherein the aryl group contains 6 or 10 carbons;

(q) aralkoxycarbonyl wherein the aralkoxy group contains from 7 to 13 carbons;

(r) alkanoyloxy containing from 2 to 3 carbons;

(s) aroyloxy wherein the aryl portion contains 6 or 10 carbons;

(t) aralkanoyloxy containing from 8 to 13 carbons;

(u) alkylsulfonamido wherein the alkyl group contains from 1 to 6 carbons;

(u)-(1) cycloalkylsulfonamido wherein the cycloalkyl portion contains 3 to 15 carbons (e.g., the cycloalkyl may be cyclohexyl, adamantyl, norbornyl), e.g., 1-adamantylsulfonylamido;

(v) aralkylsulfonamido wherein the aralkyl group contains from 7 to 13 carbons;

(w) arylsulfonamido wherein the aryl group contains 6 or 10 carbons;

(x) acylsulfonamido containing 2 to 15 carbons;

(y) alkoxycarbonyl wherein the alkoxy group contains from 1 to 3 carbons;

(z) aralkoxycarbonylamino containing from 8 to 13 carbons (e.g., benzyloxycarbonylamino);

(z)-(1) aralkylaminocarbonyloxy wherein the aralkyl group contains 7 to 12 carbons;

(z)-(2) aryloxy wherein the aryl contains 6, 10 or 12 carbons;

(z)-(3) aryloxy wherein the aryl contains 6, 10 or 12 carbons and is substituted by a member selected from aminocarbonyl, aminocarbonylalkyl where the alkyl has 1 to 3 carbons, alkoxycarbonyl having 2 to 4 carbons, and carboxy;

(aa) aryloxycarbonylamino wherein the aryloxy group contains 6 or 10 carbons;

(aa)-(1) arylaminocarbonyloxy wherein the aryl group contains 6 or 10 carbons;

(bb) alkoxycarbonylamino wherein the alkyloxy group contains from 1 to 6 carbons;

(bb)-(1) alkoxycarbonylamino wherein the alkoxy group contains 1 to 6 carbons and is optionally bonded on a carbon of an aromatic heterocyclic group as described in (gg) under $R^3$;

(bb)-(2) alkoxycarbonylamino wherein the alkoxy group contains 1 to 6 carbons substituted by an aliphatic heterocyclic group as described in (ff) under $R^3$;

(bb)-(3) aryloxyalkylcarbonylamino wherein the aryl contains 6 or 10 carbons and the alkyl has 1 to 6 carbons;

(bb)-(4) alkylaminocarbonyloxy wherein the alkyl group contains 1 to 6 carbons;

(cc) aryl containing 6 or 10 carbons (e.g., phenyl or naphthyl);

(cc)-(1) aryloxy containing 6 or 10 carbons;

(dd) aryl containing 6, 10 or 12 carbons and substituted by 1 to 3 members independently selected from the group consisting of chloro, bromo, iodo, fluoro, hydroxy, trifluoromethyl, alkyl (1 to 6 carbons), alkoxy (1 to 6 carbons), alkanoyloxy (2 to 6 carbons), alkoxycarbonyl (2 to 6 carbons), carboxy, aminocarbonylalkyl (2 to 6 carbons), aminocarbonyl, 5-tetrazolo, and acylsulfonamido (2 to 15 carbons);

(dd)-(1) aryloxy containing 6, 10 or 12 carbons and substituted by 1 to 3 members independently selected from the group consisting of chloro, bromo, iodo, fluoro, hydroxy, trifluoromethyl, alkyl (1 to 6 carbons), alkoxy (1 to 6 carbons), alkanoyloxy (2 to 6 carbons), alkoxycarbonyl (2 to 6 carbons), carboxy, acylsulfonamido (2 to 15 carbons) aminocarbonylalkyl (2 to 6 carbons), aminocarbonyl and 5-tetrazolo;

(ee) cycloalkyl containing from 3 to 15 carbons (e.g., cyclohexyl, adamantyl or norbornyl);

(ee)-(1) cycloalkyloxy containing from 3 to 15 carbons;

(ff) an aliphatic heterocyclic group of at least 5 atoms containing from 1 to 5 carbons and from 1 to 4 hetero atoms each of which is selected independently from the group consisting of nitrogen and oxygen (e.g., morpholine, piperazine), wherein the aliphatic heterocyclic group may optionally contain 1 or 2 double bond(s), which aliphatic heterocyclic group may be substituted at any nitrogen with an alkyl group containing from 1 to 6 carbons, an alkanoyl group containing from 2 to 6 carbons, an aryloxycarbonyl group wherein the aryl group contains 6, 10 or 12 carbon atoms, an aralkyloxycarbonyl group wherein the aralkyl group contains from 7 to 13 carbons or an alkoxycarbonyl group wherein the alkyl group contains from 1 to 6 carbons (e.g., morpholinyl, piperazinyl);

(ff)-(1) an aliphatic heterocyclic oxy group wherein the oxy link is bonded directly to a carbon atom of an aliphatic heterocyclic group of at least 5 atoms containing from 1 to 5 carbons and from 1 to 4 hetero atoms each of which is selected independently from the group consisting of nitrogen and oxygen, wherein the aliphatic heterocyclic group may optionally contain 1 or 2 double bond(s), which aliphatic heterocyclic group may be substituted at any nitrogen with an alkyl group containing from 1 to 6 carbons, an alkanoyl group containing from 2 to 6 carbons, an aryloxycarbonyl group wherein the aryl group contains 6, 10 or 12 carbons, an aralkyloxycarbonyl group wherein the aralkyl group contains from 7 to 13 carbons or an alkoxycarbonyl group wherein the alkyl group contains from 1 to 6 carbons;

(gg) an aromatic heterocyclic group of from 1 to 15 carbons and from 1 to 4 heteroatoms each of which is selected independently from the group consisting of sulfur, nitrogen and oxygen and which form 1 to 2 five or six-membered rings at least one of which is aromatic, and optionally, wherein up to 3 carbons of the aromatic ring(s) may be substituted with a member of the group consisting of fluoro, chloro, bromo, iodo, trifluoromethyl, methyl, alkoxy containing from 1 to 2 carbons, alkanoyl containing from 2 to 3 carbons, carboxy, aminocarbonylalkyl (b 2 to 6 carbons) and aminocarbonyl, and provided further that any nitrogen atom may be substituted by an alkyl group containing from 1 to 6 carbon atoms;

(gg)-(1) an aromatic heterocyclic oxy group wherein the oxy link is bonded directly to a carbon atom of an aromatic heterocyclic group containing (1) from 1 to 15 carbons and from 1 to 4 heteroatoms each of which is selected independently from the group consisting of sulfur, nitrogen and oxygen and (2) from 1 to 2 five or six-membered rings at least one of which is aromatic, and optionally, wherein up to 3 carbons of the aromatic ring(s) may be substituted with a member of the group consisting of fluoro, chloro, bromo, iodo, trifluoromethyl, methyl, alkoxy containing from 1 to 2 carbons, alkanoyl containing from 2 to 3 carbons, carboxy, aminocarbonylalkyl (2 to 6 carbons) and aminocarbonyl, and provided further that any nitrogen atom may be substituted by an alkyl group containing from 1 to 6 carbons;

(hh) alkylureido wherein the alkyl group contains from 1 to 6 carbon atoms;

(hh)-(1) cycloalkylureido wherein the cycloalkyl group contains 3 to 15 carbons;

(ii) aralkylureido wherein the aralkyl group contains from 7 to 13 carbons;

(jj) arylureido wherein the aryl group contains 6 or 10 carbons;

(jj)-(1) arylureido wherein the aryl group contains 6 or 10 carbons and is substituted by 1 to 3 members selected from the group consisting of chloro, bromo, iodo, fluoro, hydroxy, trifluoromethyl, alkyl (1 to 6 carbons), alkoxy (1 to 6 carbons), alkanoyloxy (2 to 6 carbons), alkoxycarbonyl (2 to 6 carbons), carboxy, acylsulfonamide (2 to 15 carbons), aminocarbonylalkyl (2 to 6 carbons), aminocarbonyl and 5-tetrazolo;

For nitrogen:

(a) alkyl of 1 to 3 carbons;

(b) alkanoyl containing from 2 to 6 carbon atoms;

(c) arylcarbonyl wherein the aryl contains 6, 10 or 12 carbons;

(d) aralkanoyl containing 8 to 14 carbons;

(e) formyl;

(f) an aliphatic heterocyclic group as defined in (ff) for the carbon substituents wherein the nitrogen is bonded directly to a carbon of the aliphatic heterocyclic group;

(g) an aromatic heterocyclic amino group as defined in (gg) for the carbon substituents wherein the nitrogen is bonded directly to a carbon of the aromatic heterocyclic group;

(IV) an aryl group containing 6 or 10 carbons;

(V) an aryl group containing 6 or 10 carbons suitably substituted by 1 to 3 members selected independently from the group consisting of fluoro, chloro, bromo, iodo, trifluoromethyl, alkyl containing from 1 to 6 carbons, alkoxy containing from 1 to 6 carbons, alkanoyloxy (2 to 6 carbons), alkoxycarbonyl containing from 2 to 6 carbons, carboxy, alkylcarbonylamino wherein the alkyl group contains 1 to 6 carbons, 5-tetrazolo, and acylsulfonamido containing from 2 to 15 carbons (e.g., 4-[(4-chlorophenyl)sulfonylaminocarbonyl]phenyl or 4-[(4-bromophenyl)sulfonylaminocarbonyl]phenyl);

(VI) a cycloalkyl group containing from 3 to 15 carbons (e.g., cyclohexyl, adamantyl, norbornyl);

(VI)-(1) a cycloalkyl group containing from 3 to 15 carbons (e.g., cyclohexyl, adamantyl or norbornyl), substituted by a member selected from the group consisting of carboxy, alkoxycarbonyl wherein the alkoxy group contains 1 to 4 carbons, 5-tetrazolo, and acylsulfonamido containing from 2 to 15 carbons;

(VII) an aliphatic heterocyclic group of at least 5 atoms containing from 1 to 5 carbons and from 1 to 4 hetero atoms each of which is selected independently from the group consisting of nitrogen and oxygen, (e.g., morpholinyl, piperazinyl), which may be substituted at any nitrogen with a member selected from the group consisting of methyl, an alkanoyl group containing from 2 to 6 carbon atoms, an aryloxycarbonyl group wherein the aryl group contains 6 or 10 carbons, an aralkoxycarbonyl group wherein the aralkyl group contains 7 carbons and an alkoxycarbonyl group containing from 2 to 3 carbons, provided that when A is OCO or NHCO, then A must be bonded to a carbon atom of the aliphatic heterocyclic group;

(VIII) an aromatic heterocyclic group of from 1 to 15 carbons and from 1 to 4 heteroatoms each of which is selected independently from the group consisting of sulfur, nitrogen and oxygen, and which form 1 to 2 five or six-membered rings at least one of which is aromatic, and optionally, wherein up to 3 carbons of the aromatic ring(s) may be substituted at any carbon atom with a member of the group consisting of fluoro, chloro, bromo, iodo, trifluoromethyl, methyl, alkoxy containing from 1 to 2 carbons, alkanoyl containing from 2 to 3 carbons, carboxy, and provided further that any nitrogen may be substituted by an alkyl group containing from 1 to 6 carbons, provided that when A is OCO or NHCO then A must be bonded to a carbon of the aromatic heterocycle;

(IX) an alkenyl group of 2 to 10 carbons, having at least one double bond;

(X) an alkenyl group of 2 to 10 carbons, having at least one double bond and substituted by a member selected from the group consisting of
(a) aryl of 6 or 10 carbons;
(b) aryl of 6 or 10 carbons substituted by 1 to 3 members selected independently from the group consisting of chloro, bromo, iodo, fluoro, hydroxy, trifluoromethyl, alkyl (1 to 6 carbons), alkoxy (1 to 6 carbons), alkanoyloxy (2 to 6 carbons), alkoxycarbonyl (2 to 6 carbons), carboxy, acylaminosulfonyl (2 to 15 carbons) and 5-tetrazolo; and
(c) ureidocarbonyl;
$R^4$ is hydrogen;
$R^C$ is hydrogen;
$R^D$ is methyl; and
A is selected from the group consisting of

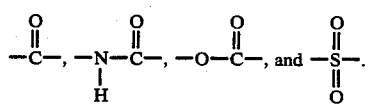

Even more particular values for the groups (when present) include
for $R^1$: isopropyl;
for $R^2$: isopropyl;
for $R^3$: phenylmethyl, 5-phenylpentyl, 2-[[4-(methoxycarbonyl)benzoyl]amino]ethyl, 2-[4-(carboxybenzoyl)amino]ethyl, 4-(methoxycarbonyl)phenyl, 4-carboxyphenyl, 4-[[(phenylsulfonyl)amino]carbonyl]phenyl, 4-[[(methylsulfonyl)amino]carbonyl]phenyl, and 4-[[[(4-chlorophenyl)sulfonyl]amino]carbonyl]phenyl;
for $R^4$: hydrogen;
for A:

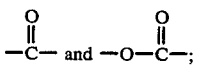

for $R^4$: $CH_2R^B$ and a group of formula II wherein X is $CH_2$, $CHR^D$ or $NR^C$ as defined above;
for $R^B$: ethyl, propyl, isopropyl, phenylmethyl, 2-phenylethyl, 1-adamantylmethyl, phenyl, and 4-isopropylphenyl;
for $R^C$: hydrogen; and
for $R^D$: methyl.

Preferred compounds of the invention include those of Examples 14, 21, 23 and 24.

The salts of the compounds of formulae Ia, Ib and Ic include pharmaceutically acceptable base or acid addition salts such as those made with a mineral acid, e.g., hydrochloric, or an organic acid such as citric, maleic, fumaric or acetic. Base-addition salts include those made with alkali metal hydroxides such as sodium hydroxide, alkali metal carbonates and bicarbonates, alkaline earth hydroxides and organic amine salts. Such salts may be prepared by dissolving the peptide derivative in a mixture of water and a water-miscible organic solvent, adding an aqueous solution of the base and recovering the salt from the aqueous solution.

The preferred compounds of the present invention are of the S configuration (i.e., that of the naturally occurring L-amino acids) at chiral centers identified by * in formulae IIIa, IIIb and IIIc below and the methods of synthesis described below provide isomers with the S configuration at the chiral center identified by symbol # or isomeric mixtures as a result of the R and S configurations at the chiral center identified by the symbol #. It is generally preferred that the compounds have the S configuration at the center identified by the symbol #.

(Formula set out on pages following Examples) IIIa (Formula set out on pages following Examples) IIIb
(Formula set out on pages following Examples) IIIc As will be appreciated by those skilled in the art, the activity of the individual isomers is not the same, and it is therefore preferred to utilize the more active isomer. The present invention includes compounds resulting from the S and/or R configuration at the chiral center labelled #.

$R^4$, $R^1$, $R^2$ and $R^3$ may have chiral centers. The present invention includes compounds of formula Ia, Ib and Ic wherein the chiral centers included in $R^4$, $R^1$, $R^2$ and $R^3$ are of the S and/or R configurations.

As will be appreciated by those skilled in the art, the difluoro ketone derivatives can exist as solvates, particularly hydrates, formulae IVa, IVb and IVc, and these are encompassed by the present invention.

(Formula set out on pages following Examples) IVa
(Formula set out on pages following Examples) IVb
(Formula set out on pages following Examples) IVc It is preferred to prepare the difluoroketone peptides of the present invention from commercially available alpha amino acids (i.e., those in which the $NH_2$ group is attached to the carbon atom next to the —COOH group). Because of this, the preferred $R^2$ moieties in the above formulae for tripeptide derivatives are those obtained from one of the following amino acids: alanine, valine, norvaline, leucine, isoleucine, norleucine, phenylalanine, tryptophan, tyrosine, asparagine, glutamine, aspartic acid, glutamic acid, lysine, threonine, serine, alphaaminobutyric acid, and phenylglycine.

According to a further feature of the invention there are provided pharmaceutical compositions comprising a pharmaceutically effective amount of at least one peptide derivative of formula Ia, Ib or Ic and a pharmaceutically acceptable diluent or carrier.

The difluoroketones of formulae Ia, Ib and Ic may be prepared as follows.

METHOD A

The key intermediate in this method for the preparation of a difluoro ketone of formula Ia, Ib or Ic is the corresponding alcohol of the following formula Va, Vb and Vc:

(Formula set out on pages following Examples) Va
(Formula set out on pages following Examples) Vb
(Formula set out on pages following Examples) Vc An alcohol of formula Va, Vb or Vc is converted to the corresponding ketone of formula Ia, Ib or Ic by an oxidative process. Methods which are useful include the use of oxalyl chloride, DMSO and a tertiary amine (see Marx, M., et al., *J. Org. Chem.*, (1984) 49, 788–793, with the best results being obtained with 10–20 equivalents of oxidizing agent), the use of acetic anhydride and DMSO, the use of chromium trioxide pyridine complex in methylene chloride, and the use of Dess-Martin periodinane [1,1,1-triacetoxy-2,1-benzoxiodol-3(3H)-one] (method of Dees, D. B. et al., *J. Org. Chem.*, (1983) 48, 4155–56).

The alcohols of formula Va, Vb or Vc may be prepared as follows:

(i) When $R^4$ is formula II with $X=NR^C$, an aldehyde of the following formula VIa, VIb or VIc:

| (Formula set out on pages following Examples) VIa |
| (Formula set out on pages following Examples) VIb |
| (Formula set out on pages following Examples) VIc | may be reacted with ethyl 2-bromo-2,2-difluoroacetate (obtained from SCM, Specialty Chemicals) and Zn in refluxing THF (see Hallinan, E. A., et al., *Tetrahedron Letters*, (1984) 25, (#22), 2301–2302) to give a compound of the following formula VIIa, VIIb or VIIc, respectively:

| (Formula set out on pages following Examples) VIIa |
| (Formula set out on pages following Examples) VIIb |
| (Formula set out on pages following Examples) VIIc | which in turn may be reacted with an amine of formula Vd:

| (Formula set out on pages following Examples) Vd | in ethanol to give the corresponding alcohol of formula VIIIa, VIIIb or VIIIc:

| (Formula set out on pages following Examples) VIIIa |
| (Formula set out on pages following Examples) VIIIb |
| (Formula set out on pages following Examples) VIIIc |

A compound of formula VIIIa, VIIIb or VIIIc may be converted into a new compound of formula VIIIa, VIIIb or VIIIc with a different value for $R^3$—A— via the formation of a corresponding compound of formula XIa, XIb or XIc:

| (Formula set out on pages following Examples) XIa |
| (Formula set out on pages following Examples) XIb |
| (Formula set out on pages following Examples) XIc | followed by reaction with the appropriate activated carbonyl or sulfonyl compound. For example, compounds of formula VIIIa, VIIIb and VIIIc when $R^3$—A is benzyloxycarbonyl, may be converted by catalytic hydrogenolysis into the amino amides of formula XIa, XIb and XIc, respectively, which in turn can be reacted with a selected activated carbonyl or sulfonyl compound (e.g., isocyanate, acid chloride, chloroformate or sulfonyl chloride) or reacted with an acid of formula $R^3COOH$ using standard peptide coupling procedures as described above to give the new compounds of formula VIIIa, VIIIb and VIIIc, respectively. Compounds of VIIIa, VIIIb and VIIIc are selected compounds of formula Va, Vb and Vc, respectively, where $R^4$ is formula II with $X=NR^C$.

The aldehydes of formula VIa, VIb or VIc may be prepared by oxidation of the corresponding alcohol of formula XIVa, XIVb or XIVc:

| (Formula set out on pages following Examples) XIVa |
| (Formula set out on pages following Examples) XIVb |
| (Formula set out on pages following Examples) XIVc |

(e.g., oxidation conditions as described in M. Marx, et al., *J. Org. Chem.*, (1984) 49, 788–793), or by hydrolysis or transacetalization of the corresponding acetal of formula XVa, XVb or XVc:

| (Formula set out on pages following Examples) XVa |
| (Formula set out on pages following Examples) XVb |
| (Formula set out on pages following Examples) XVc |

See, for example, the preparation of such compounds as described in European patent application No. 84302621.2.

Compounds of formula XIVb or XIVc (for use in making compounds of formula VIb or VIc, respectively) may be prepared by reacting an amino alcohol of formula XVI:

| (Formula set out on pages following Examples) XVI | with an appropriate free acid of formula XVIIb or XVIIc:

| (Formula set out on pages following Examples) XVIIb |
| (Formula set out on pages following Examples) XVIIc | by standard peptide coupling procedures using methods commonly known to those skilled in the art, such as those described in M. Bodanszky, *Principles of Peptide Synthesis*, Springer-Verlag, Berlin, (1984), and *The Peptides. Analysis, Synthesis and Biology* (ed. E. Gross and J. Meinhofer), Vols. 1–5, (Academic Press, New York) 1979–1983. A compound of formula XVIIb or XVIIc may be prepared by standard peptide coupling and deprotection procedures as described above. The amino alcohols of formula XVI (when not commercially available) may be prepared from the corresponding alpha-amino acids of the formula $H_2NCHR^1COOH$ by reaction with a reducing agent such as diborane. See U.S. Pat. No. 3,935,280 to Lane. A compound of formula XIVa may be prepared by reacting a compound of formula XVI with the appropriate activated carbonyl or sulfonyl compound (for example, isocyanate, carbonate, acid chloride, chloroformate or sulfonyl chloride) or reacted with an acid of formula $R^3COOH$ using standard peptide coupling procedures as described above.

Similarly, a compound of formula XVb or XVc may be prepared by reacting an amino acetal of formula XVIIIa:

| (Formula set out on pages following Examples) XVIIIa | with an appropriate acid of formula XVIIb or XVIIc by standard peptide coupling procedures; and a compound of formula XVa may be prepared by reacting a compound of formula XVIIIa with the appropriate activated carbonyl or sulfonyl compound. The amino acetal of formula XVIIIa can be prepared as described in Examples (1a–1d).

An acetal of formula XVa, XVb or XVc may be prepared, when appropriate, by an acid catalyzed acetalization of a compound of formula VIa, VIb or VIc (e.g., with triethyl orthoformate in absolute ethanol acidified with p-toluenesulfonic acid at room temperature) and converted to a new compound of formula XVa, XVb or XVc with a different value for $R^3$—A— via the formation of a corresponding compound of formula XVIIIa, XVIIIb or XVIIIc:

(Formula set out on pages following Examples) XVIIIa
(Formula set out on pages following Examples) XVIIIb
(Formula set out on pages following Examples) XVIIIc followed by reaction with the appropriate activated carbonyl or sulfonyl compound. For example, compounds of formula XVa, XVb and XVc when $R^3$—A is benzyloxycarbonyl, may be converted by catalytic hydrogenolysis into the amino acetals of formula XVIIIa, XVIIIb and XVIIIc, respectively, which in turn can be reacted with a selected activated carbonyl or sulfonyl compound (e.g., isocyanate, acid chloride, chloroformate or sulfonyl chloride) or reacted with an acid of formula $R^3$COOH using standard peptide coupling procedures as described above to give the new compounds of formula XVa, XVb and XVc, respectively.

An alternate method for the preparation of a compound of formula VIIIb or VIIIc from a compound of formula VIIb or VIIc, respectively, comprises reacting a compound of formula VIIb or VIIc with about 1.25 equivalents of 1N NaOH in CH$_3$OH to give compounds of formula IXb or IXc, respectively:

(Formula set out on pages following Examples) IXb
(Formula set out on pages following Examples) IXc followed by reaction of the compound of formula IXb or IXc with a compound of formula Vd using (a) HOBT, WSCDI and THF or (b) tetramethylguanidine and CHCl$_3$ at 0° C. to room temperature to obtain the particular compound of formula VIIIb or VIIIc. (See R. H. Abeles, et al., *Biochemistry*, (1985) 24, 1813).

(ii) When $R^4$ is formula II with X=CH$_2$, an alcohol of formula Xa, Xb or Xc (where Xa, Xb and Xc are selected members of formula Va, Vb and Vc, respectively, where $R^4$ is formula II with X=CH$_2$):

(Formula set out on pages following Examples) Xa
(Formula set out on pages following Examples) Xb
(Formula set out on pages following Examples) Xc may be prepared by reacting a compound of formula IXa (where compound IXa may be prepared from compound VIIa above as described for IXb and IXc) IXb or IXc, respectively, (Formula set out on pages following Examples) IXa
(Formula set out on pages following Examples) IXb
(Formula set out on pages following Examples) IXc with N,O-dimethylhydroxyamine hydrochloride, WSCDI, HOBT and N-methylmorpholine in CH$_2$Cl$_2$. (See *Int. J. Protein Res.*, (1985) 26, 236–241) to obtain a compound of formula XIIa, XIIb or XIIc, respectively:

(Formula set out on pages following Examples) XIIa
(Formula set out on pages following Examples) XIIb (Formula set out on pages following Examples) XIIc followed by reacting a compound of formula XIIa, XIIb or XIIc with a Grignard reagent of formula $R^B$CH$_2$MgBr to form a compound of formula Xa, Xb or Xc, respectively.

(iia) Similarly, when $R^4$ is formula II with X=CHR$^D$, an alcohol of formula Va, Vb or Vc, wherein $R^4$ is formula II with X=CHR$^D$ may be prepared by reacting a corresponding compound of formula XIIa, XIIb or XIIc with a Gringard reagent of formula $R^B R^D$CHMgBr.

(iii) when $R^4$ is CH$_3$, CH$_2$R$^B$ or CHR$^B$R$^D$, compounds of formula Va, Vb or Vc may be made as follows:

Compounds of formula Vc, where $R^4$ is CH$_3$, CH$_2$R$^B$ or CHR$^B$R$^D$, may be prepared according to the following Scheme 1:

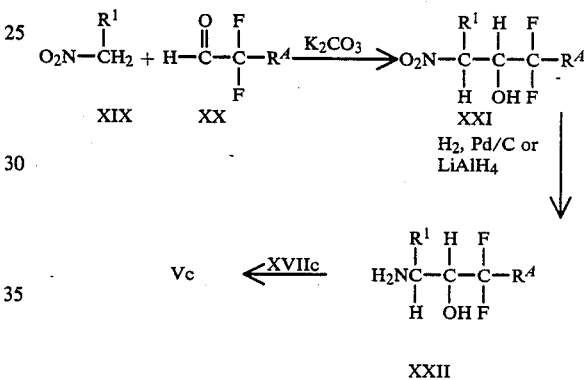

Scheme 1

For use as shown in Scheme 1, a starting aldehyde of formula XX may be prepared from the corresponding alkyl ester of formula XXIV:

(Formula set out on pages following Examples) XXIV wherein $R^X$=(1–3C)alkyl, (for example, ethyl), by a direct reduction (for example, with diisobutylaluminum hydride) or by reduction with NaBH$_4$ in ethanol at room temperature to the corresponding alcohol followed by oxidation (oxalyl chloride, DMSO) to the aldehyde as described by Marx and Tidwell, supra.

A difluoroester of formula XXIV may be prepared from an alpha-ketoester of formula XXV (Formula set out on pages following Examples) XXV by reaction with diethylaminosulfurtrifluoride (DAST). See B. Erni and H. G. Khorana, *J. Amer. Chem. Soc.*, (1980) 102, 3888. The alpha-ketoesters of formula XXV, when not commercially available, may be prepared from the corresponding alpha-amino acids according to the procedure of: F. Weygand et al., *Leibigs. Ann. Chem. Bd.*, (1962) 658, 128, followed by an esterification. Alternatively, an alpha-ketoester of formula XXV may be prepared according to the general procedure of reacting an alkyl 1,3-dithiane-2-carboxylate (for example, the ethyl compound) with a bromide of formula BrR$^A$ as described in Eliel, D. H., et al., *J. Org. Chem.*, (1972) 37, 505.

An aldehyde of formula XX may be reacted with a nitro compound of formula XIX (O$_2$N—CH$_2$—R$^1$) and K$_2$CO$_3$ to give a compound of formula XXI. A compound of formula XXI may be reduced (e.g., by hydrogenation or LiAlH$_4$) to yield a compound of formula XXII. A compound of formula XXII may be reacted with a compound of formula XVIIc using standard peptide coupling conditions to give the key alcohol intermediate, a compound of formula Vc.

Compounds of formula Va where R$^A$ is CH$_3$, CH$_2$R$^B$ or CHR$^B$R$^D$ may be prepared from compounds of formula XXII by reacting compounds of formula XXII with the appropriate activated carbonyl or sulfonyl compounds.

Compounds of formula Vb, where R$^A$ is CH$_3$, CH$_2$R$^B$ or CHR$^B$R$^D$ may be prepared from compounds of formula XXII by reacting compounds of formula XXII with appropriate compounds of XVIIb using standard peptide coupling conditions as described above for compounds of Vc.

METHOD B

A compound of formula Ia, Ib or Ic where R$^A$ is formula II with X=NR$^C$ may be prepared from the corresponding ester, such as the ethyl ester of formula XXVIa, XXVIb or XXVIc:

| |
|---|
| (Formula set out on pages following Examples) XXVIa |
| (Formula set out on pages following Examples) XXVIb |
| (Formula set out on pages following Examples) XXVIc | either directly by heating the ester with an appropriate amine of formula Vd in ethanol to afford the corresponding compound of formula Ia, Ib or Ic or, alternatively, indirectly by first hydrolyzing the ester to the corresponding acid of formula XXVIIa, XXVIIb, or XXVIIc:

| |
|---|
| (Formula set out on pages following Examples) XXVIIa |
| (Formula set out on pages following Examples) XXVIIb |
| (Formula set out on pages following Examples) XXVIIc |

(using a similar method to that described above for the hydrolysis of a compound of formula VIIc to a compound of formula IXc), followed by coupling the acid with an amine of formula Vd (using similar conditions to those described above for the conversion of IXc to VIIIc) to afford the corresponding compound of formula Ia, Ib or Ic. A starting ester of formula XXVIa, XXVIb or XXVIc may be obtained by oxidation of the corresponding alcohol of formula VIIa, VIIb or VIIc using one of the oxidation methods described in Method A.

METHOD C

A compound of formula Ia, Ib or Ic where R$^2$ or R$^3$ contains a carboxy group may be prepared by decomposing the ester group of a corresponding compound of formula Ia, Ib or Ic where R$^2$ or R$^3$ contains an ester group. The ester groups contained by R$^2$ and R$^3$ of compounds of formula Ia, Ib and Ic described above include aryloxycarbonyl wherein the aryl group contains 6, 10 or 12 carbons, aralkoxycarbonyl wherein the aralkoxy group contains from 7 to 13 carbons, and alkoxycarbonyl wherein the particular alkoxy group contains from 1 to 3, 1-4, 1-5 or 1-6 carbons.

It will be appreciated that the decomposition can be performed using any one of a variety of procedures well known in the art of organic chemistry. Thus, it may be carried out, for example, by conventional hydrolysis under acid or base conditions, adjusted as necessary to minimize any hydrolytic removal of other functional groups in the molecule. Also, when the ester is an aralkoxycarbonyl group, such as benzyloxycarbonyl, it may be possible to carry out the decomposition by reductive means, for example, by the use of hydrogen at about atmospheric pressure in the presence of a suitable catalyst, such as palladium or platinum, conveniently on charcoal as a support.

A preferred method for decomposing an ester of formula Ia, Ib or Ic comprises reacting the ester with a suitable base, for example, an alkali or alkaline earth metal hydroxide or carbonate (such as lithium hydroxide, potassium hydroxide, sodium hydroxide, calcium hydroxide or potassium carbonate) in a suitable, aqueous solvent or diluent, for example, water, optionally together with a water-miscible organic cosolvent, such as methanol, and conveniently at or near ambient temperature. When such a method is employed, the resultant carboxylic acid of formula Ia, Ib or Ic where R$^2$ or R$^3$ contains a carboxy group is initially obtained as the corresponding salt of the base used for the hydrolysis and may be isolated as such or converted to the free acid form by a conventional acidification procedure.

METHOD D

A compound of formula Ia, Ib or Ic where R$^2$ or R$^3$ contains an acylsulfonamide group of the sulfonamidocarbonyl type may be prepared by reacting the corresponding compound of formula Ia, Ib or Ic where R$^2$ or R$^3$ contains a carboxy group with an appropriate sulfonamide in the presence of a dehydrating agent, for example, with 1-ethyl-3-(3-dimethylaminopropyl)carbodiimide, or with a hydrochloride or hydrobromide salt thereof optionally together with an organic base, for example, 4-(dimethylamino)pyridine, in the presence of a suitable solvent or diluent, for example, dichloromethane, at a temperature in the range of, for example, 10° to 50° C., but preferably at or near ambient temperature.

Also, it may be desired to optionally use a protecting group during all or portions of the above described processes; the protecting group may then be removed when the final compound is to be formed. (See Greene, T. W., *Protective Groups in Organic Synthesis*, Wiley-Intersciences, New York (1981).)

When a pharmaceutically acceptable salt is desired or required, it may be obtained using standard procedures well known in the art, for example, by further reacting a suitably acidic compound of formula Ia, Ib or Ic with a suitable base affording a physiologically acceptable cation or by further reacting a sufficiently basic compound of formula Ia, Ib or Ic with a suitable acid affording a physiologically acceptable anion.

INHIBITION MEASUREMENTS

The ability of compounds of the invention to act as elastase inhibitors may be initially determined by the ability of a compound of the invention to inhibit the action of human leukocyte elastase (HLE) on a low molecular weight peptide substrate. The potency of an inhibitor is evaluated by obtaining a kinetic determination of the dissociation constant, $K_i$, of the complex formed from the interaction of the inhibitor with HLE. The substrate used was the anilide methoxysuccinyl-L-alanyl-L-alanyl-L-prolyl-L-valine-p-nitroanilide as described by K. Nakajima et al. in *J. Biol. Chem.*, (1979) 254, 4027-4032 and by T. Teshima et al. in *J. Biol. Chem.*, (1982) 257, 9, 5085-5091. The HLE enzyme used in these studies may be obtained from Elastin Products of St. Louis, Mo. or can be purified according to B. R. Viscarello et al. in *Preparative Biochemistry*, (1983) 13, 57-67 as follows, all work being done in a cold room at 4° C.

Salt Extraction-DNase Treatment: The starting material, 193 g of purulent sputum, was homogenized with 200 ml of cold distilled water and centrifuged at 30,000× gravity for 20 min. at 4° C. The supernatant was discarded and the pellet extracted with high salt and treated with DNase as per the method of D. Y. Twumasi et al. in *J. Biol. Chem.*, (1977) 252, 1917-1926. Chromatography on Elastin Agarose: The precipitate from the DNase digest was taken up in two 40 ml portions of 50 mM Tris, 1.0M NaCl, pH 8; the suspension was centrifuged and the resulting supernatant applied directly to a column of soluble elastin-Sepharose 4B (2.5×20 cm). The column was washed with equilibrating buffer (50 mM Tris, 50 mM NaCl, pH 8.0) until the optical density at 280 nm ($OD_{280}$) of the eluate returned to baseline. Additional contaminating protein was eluted with two column volumes of 50 mM acetate, 1.0M NaCl, pH 5.0. Elastase and cathepsin G (HLC-G) were finally eluted with 50 mM acetate, 1.0M NaCl, 20% DMSO, pH 5.0. The column was developed at 6 ml/min with the collection of 10 ml fractions. The active fractions were pooled, dialyzed vs. two 6 liter changes of 50 mM acetate, 0.1M NaCl, pH 5.5, and concentrated to 40 ml on an Amicon ® ultrafiltration unit (YM-10 membrane). CM-Chromatography: The concentrated active fraction was applied to a column of CM-Sephadex ® C-50 (2.2×10 cm) previously equilibrated with 50 mM acetate, 0.1M NaCl, pH 5.5 and the column then washed with this buffer to remove contaminating protein. Elution was continued with 50 mM acetate, 0.2M NaCl, pH 5.5 and resulted in the displacement of a peak of activity assayed against Bz-L-Phe-L-Val-L-Arg-pNA. HLE was next eluted with the acetate buffer containing 0.45M NaCl, while elution of HLC-G required the presence of 1.0M NaCl in the buffer as described by R. Martodam et al. in *Preparative Biochemistry*, (1979) 9, 15-31. This column was developed at 30 ml/hr with the collection of 5.5 ml fractions. From the thus purified HLE, a standard rate of production of p-nitroaniline was measured at 25° C. spectrophotometrically in the visible spectrum at 410 nanometers with automatic data acquisition from a Cary 210 spectrophotometer obtained from Varian Associates. Reactions were initiated by injection of 10 microliters of the HLE solution into a 3 milliliter cuvette containing 2.89 milliliters of buffer (10 millimolar sodium phosphate, 500 millimolar NaCl, pH 7.6), 50 microliters substrate solution in DMSO, and 50 microliters of DMSO. Initial, steady-state reaction velocities of p-nitroaniline production were calculated by a fit of the experimental data to a linear dependence on time by linear least squares. This velocity, determined with no inhibitor present, was used as a standard in the calculation of inhibitor $K_i$ values.

As a general rule, the peptide derivatives of the present invention were found to be "slow-binding" inhibitors of HLE and therefore required special methods of analysis to accurately determine $K_i$ values for their inhibition of HLE (see Williams, J. W. and Morrison, J. F., *Meth. Enz.* (1979) 63, 437 for a description of these methods.) In a typical experiment, 2.89 ml of buffer (10 millimolar sodium phosphate, 500 millimolar sodium chloride, pH 7.6), 50 microliters of inhibitor solution in DMSO, and 50 microliters of substrate solution in DMSO were added to a 3 milliliter cuvette. The cuvette was stoppered, inverted several times to mix its contents and maintained at (25° C.) in the spectrophotometer. After a period of five minutes to allow the reaction solution to come to thermal equilibrium, 10 microliters of stock enzyme solution were added to the cuvette to initiate the reaction. Duplicate or triplicate runs were done at zero inhibitor concentration and at least three non-zero inhibitor concentrations. $K_i$ values were calculated according to methods outlined in the above reference by Williams and Morrison. The $K_i$ values for selected compounds were less than $10^{-7}M$.

ANIMAL MODELS

Animal models of emphysema include intratracheal (i.t.) administration of an elastolytic protease to cause a slowly progressive, destructive lesion of the lung. These lesions are normally evaluated a few weeks to a few months after the initial insult. However, these proteases also induce a lesion that is evident in the first few hours. The early lesion is first hemorrhagic, progresses to an inflammatory lesion by the end of the first 24 hours and resolves in the first week post insult. To take advantage of this early lesion, the following model was used.

Hamsters are first lightly anesthetized with methohexital sodium (Brevital ® from Eli Lilly). Phosphate buffered saline (PBS) pH 7.4, either alone or containing 400 µg of human leukocyte elactase (HLE), is then administered directly into the trachea. Twenty-four hours later the animals are killed and the lungs removed and carefully trimmed of extraneous tissue. Following determination of wet lung weight, the lungs are lavaged with PBS and total lavagable red and white cells recovered are determined. The values for wet lung weights, total lavageable red cells and total lavageable white cells are elevated in a dose-dependent manner following administration of HLE. Compounds that are effective elastase inhibitors can prevent or diminish the severity of the enzyme-induced lesion resulting in lower wet lung weight and reduced values for total lavageable cells, both red and white, relative to administration of HLE alone. Compounds can be evaluated by administering them either with or at various times prior to administration of HLE to determine their utility in preventing an HLE lesion. Compounds of this invention produced statistically significant reductions in wet lung weight and total lavageable cells relative to HLE alone.

Compounds of the present invention exhibited activity in at least one of the tests described above under Inhibition Measurement or Animal Model. It should be noted that there was not always a direct correlation between the activities of the compounds measured as $K_i$ values in the Inhibition Measurement test and the reduced values for total lavageable cells and wet lung weights relative to the administration of HLE alone obtained in the Animal Model test. It is thought that the Animal Model test is more predictive of the activity of such compounds in the treatment of emphysema.

Pharmacokinetics: Male Syrian hamsters (80 to 120 g) are injected intravenously with the test compound. Prior to injection and at varying time periods thereafter, they are lightly anesthetized with ether and blood samples of approximately 0.2 ml each are withdrawn by cardiac puncture. The blood is expressed into 2 ml centrifuge tubes and allowed to clot for one hour. The sample is then centrifuged and the serum removed.

Drug levels are determined by first inactivating endogenous elastase inhibitors by incubation of 50 microliters of serum with an equal volume of buffer containing 5 mg/ml bovine pancreatic trypsin for 5 min. The trypsin inactivated serum (10 microliters) is then added to a 0.52 ml cuvette containing buffer made 20 nM with respect to HLE. After an additional 30 min. incubation, the reaction is started by the addition of substrate (350 microliters) (MeOSuc-L-Ala-L-Ala-L-Pro-L-Val-pNA, 1.6 mM) and the reaction monitored spectrophotometrically at a wavelength of 410 nM. For comparative purposes, serum persistence of the test compounds is determined in the following manner:

Percent inhibition of serum samples is calculated as follows:

$$\text{percent inhibition} = \frac{V_o - V_i}{V_o} \times 100$$

The compounds of the present invention may be administered to a warm-blooded animal in need thereof, particularly a human, for the treatment of conditions of pulmonary emphysema, atherosclerosis, rheumatoid arthritis, and osteo arthritis, but in particular for emphysema. The mode of administration may be oral, parenteral, including the subcutaneous deposit by means of an osmotic pump, or via a powdered or liquid aerosol. These may be conventionally formulated in an oral or parenteral dosage form by compounding about 10 to 250 mg per unit dosage with conventional vehicle, excipient, binder, preservative, stabilizer, flavor or the like as called for by accepted pharmaceutical practice e.g. as described in U.S. Pat. No. 3,755,340. For parenteral administration, a 1 to 10 ml intravenous, intramuscular or subcutaneous injection would be given containing about 0.02 to 10 mg/kg of body weight of a compound of the invention 3 or 4 times daily. The injection would contain a compound of the invention in an aqueous isotonic sterile solution or suspension optionally with a preservative such as phenol or a solubilizing agent such as ethylenediaminetetraacetic acid (EDTA). In a powdered aerosol, compounds of the invention may be administered in the same manner as cromolyn sodium via a Spinhaler ® turbo-inhaler device obtained from Fisons Corp. of Bedford, Mass. at a rate of about 0.1 to 50 mg per capsule, 1 to 8 capsules being administered daily for an average human. Each capsule to be used in the Spinhaler ® contains the required amount of a compound of the invention with the remainder of the 20 mg capsule being a pharmaceutically-acceptable carrier such as lactose. In a liquid aerosol, the compounds of the invention are administered at the rate of about 100 to 1000 micrograms per "puff" or activated release of a standard volume of propellant. The liquid aerosol would be given at the rate of 1 to 8 puffs per day with variation in dosages due to the severity of the condition being treated, the weight of the patient and the particle size distribution of the aerosol since smaller particles will achieve greater lung penetration. Propellants, e.g., a fluorinated hydrocarbon or isobutane, containers, valves and actuators for liquid aerosols are described by L. Lachman et al. in "The Theory and Practice of Industrial Pharmacy", Lea and Febiger, Philadelphia (1976).

In the following Examples and throughout the specification, the following abbreviations are used: atm (atmospheres) with $1.013 \times 10^5$ Pascals = 1 atm; bp (boiling point); °C. (degrees Centigrade); g (grams); hr (hours); mg (milligrams); min (minutes); ml (milliliters); mmol (millimoles); mp (melting point); N (normal); nm (nanometers); nM (nanomolar); $R_f$ (relative mobility in TLC); TLC (thin layer chromatography); DCC (dicyclohexylcarbodiimide); DMF (dimethylformamide); DMSO (dimethyl sulfoxide); Et$_2$O (diethyl ether); EtOAc (ethyl acetate); HOAc (acetic acid); WSCDI (water soluble carbodiimide; 1-ethyl-3-(3-dimethylaminopropyl)carbodiimide hydrochloride); Bz (benzoyl); HOBT (1-hydroxybenzotriazole); MeOH (methyl alcohol); Pd/C (palladium on charcoal catalyst); pNA (paranitroanilide); DMAP (4-dimethylaminopyridine); φ (phenyl group); NMM (N-methylmorpholine); THF (tetrahydrofuran); CBZ (benzyloxycarbonyl); t-BOC (tertiarybutyloxycarbonyl); $t_R$ (HPLC retention time in min); HPLC (high performance liquid chromatography); TEA (triethylamine); TFA (trifluoroacetic acid); Ac$_2$O (acetic anhydride); RT (room temperature); e.g. (for example); supra (above); DAST (diethylaminosulfurtrifluoride); vs. (versus); Dibal (diisobutylaluminum hydride); and Zorbax ® ODS analytical column (4.6 mm×25 cm). In addition, C, H, N, etc. (the conventional symbols for the elements) are used, and conventional abbreviations for amino acids, e.g. proline (Pro), valine (Val) etc. are also used. It is to be understood that generic terms such as "(1-10C)alkyl" include both straight and branched chain alkyl radicals, but references to individual alkyl radicals such as "propyl" include only the straight chain ("normal") radical, branched chain isomers such as "isopropyl" being specifically referred to. $^1$H NMR data is given for values of delta using tetramethylsilane as an internal standard.

EXAMPLE 1

[3,3-Difluoro-1-(1-methylethyl)-2,4-dioxo-4-[(phenylmethyl)-amino]butyl]carbamic acid phenylmethyl ester a. N—Benzyloxycarbonyl-L—valinol (Formula XIVa, $R^3A = \phi CH_2OC\underset{\overset{\|}{O}}{-}$, $R^1 = CH(CH_3)_2$)

Benzyl chloroformate (91.0 g, 0.532 mol, 95% purity) was added dropwise over a period of 1 hr to a precooled (0° C.) solution of L-valinol (50.0 g, 0.484 mol) and triethylamine (60.0 g, 0.6 mol) in CHCl$_3$ (1500 ml). The reaction mixture was stirred for 1 hr. at 0° C. and then allowed to warm to room temperature over 2 hr. The reaction mixture was concentrated under vacuum. EtOAc (1500 ml) was added to the resulting residue and the organic solution was sequentially washed with aqueous 1N NaOH and brine. The organic phase was dried over MgSO$_4$, and then filtered and concentrated under vacuum. The resulting residue was purified by flash chromatography on a column of silica gel (6 cm×30 cm) using a stepwise gradient of Et$_2$O:hexane (1:5) followed by pure Et$_2$O to give the product (91.4 g)

as a white waxy solid; TLC, $R_f=0.23$, silica gel, hexane:Et$_2$O (50:50).

N—Benzyloxycarbonyl-L—valinal (Formula VIa, $R^3A = \phi CH_2OC-$, $R^1 = CH(CH_3)_2$)    b.
                        $\parallel$
                        O A solution of DMSO (107.2 g, 1.372 mol) in CH$_2$Cl$_2$ (150 ml) was added dropwise over 0.5 hr. to a precooled ($-60°$ C.), stirred solution of oxalyl chloride (87.1 g, 0.686 ml) in CH$_2$Cl$_2$ (800 ml) under a nitrogen atmosphere. The temperature of the mixture rose to $-45°$ C. The reaction mixture was then warmed to $-30°$ C. A solution of the product of Example 1a (81.5 g, 0.343 mol) in CH$_2$Cl$_2$ (300 ml) was added dropwise over 45 min at $-30°$ C. The reaction mixture was stirred for 50 min at $-25°$ C., cooled to $-40°$ C. and a solution of diisopropylethyl amine (177.4 g, 1.372 mol) in CH$_2$Cl$_2$ (250 ml) was added dropwise over 45 min at $-40°$ C. The reaction mixture was stirred for 1 hr as it warmed to room temperature. The reaction mixture was diluted with CH$_2$Cl$_2$ (1500 ml) and the organic phase was washed with aqueous 1N HCl and then concentrated under vacuum to give the product (98 g) as a green oil which was used immediately without further purification; TLC, $R_f=0.48$, silica gel, hexane:Et$_2$O (50:50).

N—Benzyloxycarbonyl-L—valinal diethylacetal (Formula XVa, $R^3A = \phi CH_2OC-$, $R^1 = CH(CH_3)_2$)    c.
                         $\parallel$
                         O Triethyl orthoformate (700 g, 4.723 mol), absolute EtOH (800 ml) and p-toluenesulfonic acid monohydrate (5.0 g, 0.026 mol) were added to a portion of the product of Example 1b (81 g, 0.343 mol). The mixture was stirred for 10 min at room temperature and then concentrated under vacuum. The resulting residue was dissolved in Et$_2$O and washed with saturated aqueous NaHCO$_3$. The organic phase was dried over Na$_2$SO$_4$, filtered and concentrated under vacuum to give a crude product. This product was purified by flash chromatography with silica gel using a stepwise gradient of hexane through mixtures of CH$_2$Cl$_2$:hexane to EtOAc:CH$_2$Cl$_2$ (30:70) to give the product as a pale yellow oil; TLC, $R_f=0.21$, silica gel, CH$_2$Cl$_2$:petroleum ether (50:50).

d. L-Valinal diethylacetal (Formula XVIIIa, $R^1=CH(CH_3)_2$)

A mixture of the product of Example 1c (147.8 g, 0.478 mol) and 10% Pd/C (10 g) in EtOAc (1500 ml) was stirred under H$_2$ (1 atm.) until 2500 ml of H$_2$ were consumed. Twice during this time the reaction was interrupted and 10% Pd/C (10 g) was added. The reaction mixture was then filtered through a pad of diatomaceous earth. 10% Pd/C (10 g) was added and the reaction mixture was stirred until 10.92 liters of H$_2$ were consumed. The reaction mixture was filtered through diatomaceous earth and the filtrate was concentrated under vacuum to give the product (78.8 g) as a pale yellow oil; [alpha]$_D^{25}=+7.8$.

(Formula VIIa, $R^3A = \phi CH_2OC-$, $R^1 = CH(CH_3)_2$)    e.
                        $\parallel$
                        O A portion of the compound of Example 1b (3.0 g, 12.7 mmol), ethyl 2-bromo-2,2-difluoroacetate (2.58 g, 12.7 mmol) and Zn dust (1.22 g) were refluxed in THF (30 ml) for 0.5 hr. Additional Zn dust (1.22 g) and ethyl 2-bromo-2,2-difluoroacetate (2.58 g, 12.7 mmol) were added and the resulting solution refluxed for an additional hour. The solution was cooled to room temperature and ethyl acetate (150 ml) was added. The ethyl acetate solution was sequentially washed with 1M KHSO$_4$ and brine. The organic layer was dried with Na$_2$SO$_4$, filtered, and the solvent removed under reduced pressure to give a crude product (2.4 g). The product was purified by flash chromatography on silica gel with an eluent of ethyl acetate:hexane (35:65) to give the final product (0.9 g) as an oil; TLC, $R_f=0.55$, silica gel, ethyl acetate:hexane (35:65).

(Formula Va, $R^3A = \phi CH_2OC-$,    f.
              $\parallel$
              O $R^1 = CH(CH_3)_2$, $R^4 = CONHCH_2\phi$)

A portion of the product of Example 1e, (0.5 g, 0.7 mmol), benzylamine (240 ml) and ethanol (20 ml) were heated at 65° C. for 2 hr. The resulting solution was cooled to room temperature and the solvent removed under reduced pressure to give a crude product. The product was purified by flash chromatography on silica gel with an eluent of ethyl acetate:chloroform (15:85) to give the product (0.56 g) as a clear oil; TLC, $R_f=0.5$, silica gel, ethyl acetate:chloroform (15:85).

(Formula Ia, $R^3A = \phi CH_2OC-$,    g.
              $\parallel$
              O $R^1 = CH(CH_3)_2$, $R^4 = CONHCH_2\phi$)

The product from Example 1f (0.56 g, 1.34 mmol), acetic anhydride (10 ml) and dimethylsulfoxide (10 ml) were stirred at room temperature under N$_2$ for 24 hr. Ice water (100 ml) was added and the solution stirred for 3 hr. The solid precipitate (0.3 g) was collected and washed with water and petroleum ether. The solid product had a melting point of 78°–80° C.

Analysis calculated for C$_{22}$H$_{24}$N$_2$O$_4$F$_2$: C, 63.1; H, 5.78; N, 6.69. Found: C, 62.77, 62.98; H, 5.67, 5.71; N, 6.34, 6.20.

EXAMPLE 2

N-[3,3-Difluoro-1-(1-methylethyl)-2,4-dioxo-4-[(phenylmethyl)amino]butyl]-1-(1-oxo-6-phenylhexyl)-2-pyrrolidinecarboxamide a. (Formula XIVb, $R^3A = \phi CH_2OC-$, $R^1 = CH(CH_3)_2$)
                              $\parallel$
                              O Isobutyl chloroformate (5.4 g, 0.039 mol) was added to a solution of N-benzyloxycarbonyl-L-proline (9.8 g, 0.039 mol) and N-methylmorpholine (4.0 g, 0.039 mol) in dry THF (150 ml) at $-20°$ C. under an N$_2$ atmosphere. The reaction was stirred for 10 min and then cooled to $-40°$ C. A solution of L-valinol (4.06 g, 0.039 mol) in dry THF (75 ml) was added dropwise. The reaction was allowed to warm to room temperature and stirred overnight. The reaction was filtered and the solvents removed under reduced pressure. The residue was taken up in EtOAc and washed successively with aqueous 1N HCl, saturated aqueous NaHCO₃ and brine. The organic phase was dried over Na₂SO₄, filtered and concentrated to give the product (12.64 g) as a white solid; TLC, R_f=0.2, silica gel, MeOH:CHCl₃ (5:95).

b. (Formula VIb, R³A = φCH₂OC(=O)—, R¹ = CH(CH₃)₂)

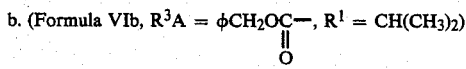

A solution of DMSO (10.3 g, 0.132 mol) in dry CH₂Cl₂ (40 ml) was added dropwise to a stirred solution of oxalyl chloride (8.4 g, 0.066 mol) in dry CH₂Cl₂ (100 ml) cooled to −60° C. under an N₂ atmosphere. The reaction was then warmed to −25° C. and a solution of the product of Example 2a (11.0 g, 0.033 mol) in dry CH₂Cl₂ (40 ml) was added dropwise. The reaction was stirred for 30 min and a solution of diisopropylethylamine (17.0 g, 0.132 mol) in dry CH₂Cl₂ (25 ml) was added dropwise in such a manner as to maintain the temperature below −25° C. The reaction was warmed to room temperature, diluted with CH₂Cl₂ (300 ml) and washed with aqueous 1N HCl and then brine. The organic phase was dried over Na₂SO₄, filtered and concentrated under vacuum to give the crude product (10.96 g) as a yellow oil which was used immediately in the next reaction Example 2c; TLC, R_f=0.56, silica gel, MeOH:CHCl₃ (5:95).

c. (Formula XVb, R³A = φCH₂OC(=O)—, R¹ = CH(CH₃)₂)

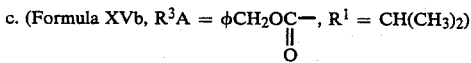

p-Toluenesulfonic acid (0.475 g, 0.0025 mol) was added to a solution of the product of Example 2b (10.96 g, 0.033 mol) and triethylorthoformate (48.8 g, 0.330 mol) in absolute EtOH (75 ml). The reaction was stirred for 15 min and then concentrated under vacuum. The residue was taken up in EtOAc and sequentially washed with saturated aqueous NaHCO₃ and brine. The organic phase was dried over Na₂SO₄, filtered and concentrated to give a crude product as a yellow oil. The product was purified by flash chromatography on silica gel using a gradient starting with CHCl₃ and ending with MeOH:CHCl₃ (2.5:97.5) as eluent to give the product (13.18 g) as a pale yellow oil; TLC, R_f=0.54, silica gel, MeOH:CHCl₃ (2:98).

d. (Formula XVIIIb, R¹=CH(CH₃)₂)

A solution of product prepared by the method of Example 2c (12.0 g, 0.0296 mol), absolute EtOH (125 ml) and 10% Pd/C (1.2 g, 0.0296 mol) was stirred under an atmosphere of H₂ for about 4 hr. Additional 10% Pd/C (1.2 g) was added and the reaction stirred overnight under 1 atmosphere of H₂. Another portion of 10% Pd/C (1.2 g) was added and the reaction stirred under 1 atmosphere for 5 hr. Another portion of 10% Pd/C (1.2 g) was added and the reaction was stirred overnight under 1 atmosphere of H₂. The reaction was filtered through diatomaceous earth and concentrated under vacuum. The residue was taken up in absolute EtOH (250 ml); 10% Pd/C (2.0 g) was added and the reaction stirred under 1 atmosphere of H₂ for 2.5 hours. The reaction was filtered and concentrated under vacuum to give the product (7.42 g) as a yellow glass; TLC, R_f=0.44, silica gel, CH₃OH:CHCl₃ (10:90).

e. (Formula XVb, R³A = φ(CH₂)₅C(=O)—, R¹ = CH(CH₃)₂)

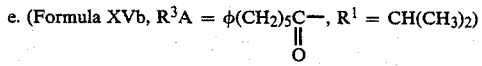

A solution of phenylhexanoic acid (1.27 g, 1.4 mmol), carbonyldiimidazole (CDI) (0.230 g, 1.4 mmol) and THF (20 ml) was stirred at room temperature under N₂ for 1 hour. A portion of the product of Example 2d (0.38 g, 1.42 mmol) was added and the resulting solution was stirred at room temperature overnight. Saturated NaHCO₃ and H₂O were added and the solution was stirred for 1 hour. The solvent was removed under reduced pressure and ethyl acetate (50 ml) was added. The organic layer was collected, dried with Na₂SO₄, filtered and the solvent removed under reduced pressure to give a crude product as a pale yellow oil; The product was purified by flash chromatography on silica gel with an eluent of methanol:chloroform (3:97) to give the final product (0.35 g) as a clear oil; TLC, R_f=0.45, silica gel, ethyl acetate:hexane (66:33).

f. (Formula VIb, R³A = φ(CH₂)₅C(=O)—, R¹ = CH(CH₃)₂)

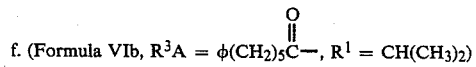

A solution of the product of Example 2e (0.33 g, 0.74 mmol), p-toluenesulfonic acid (0.14 g, 0.75 mmol) and acetone (10 ml) was stirred at room temperature for 3 hr. The solvent was then removed under reduced pressure and the residue dissolved in ethyl acetate. The ethyl acetate solution was washed with 5% aqueous NaHCO₃ and brine and the organic layer was dried over MgSO₄, filtered and the solvent removed under reduced pressure to give the product (0.26 g) as a clear oil; TLC, R_f=0.28, silica gel, EtOAc:hexane (2:1).

g. (Formula VIIb, R³A = φ(CH₂)₅C(=O)—, R¹ = CH(CH₃)₂)

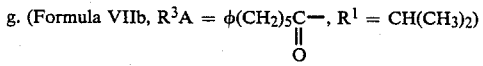

A solution of the product of Example 2f (0.26 g, 0.7 mmol), Zn dust (0.077 g, 0.88 mmol), ethyl 2-bromo-2,2-difluoroacetate (0.18 g, 0.88 mmol) and THF (10 ml) was stirred at reflux for 0.5 hours. Additional portions of Zn dust (0.077 g, 0.88 mmol) and ethyl 2-bromo-2,2-difluoroacetate (0.18 g, 0.88 mmol) were added and the solution stirred at reflux for an additional 2 hr. The solution was cooled to room temperature and ethyl acetate (60 ml) was added. The resulting solution was washed with 1M KHSO₄ and brine and the organic layer was collected, dried with Na₂SO₄, filtered and the solvent removed under reduced pressure to give the product (0.350 g) as an oil; TLC, R_f=0.6, silica gel, ethyl acetate:hexane (2:1).

h. (Formula Vb, R³A = φ(CH₂)₅C(=O)—, R¹ = CH(CH₃)₂,

R⁴ = CONHCH₂φ)

A solution of the product of Example 2g (0.35 g, 0.7 mmol), benzylamine (0.3 ml, 2.8 mmol) and ethanol (10 ml) was stirred at 80° C. under N₂ for 4 hr and then stirred at RT overnight. Ethanol was removed under reduced pressure to give a crude product as a yellow oil. The product was purified by flash chromatography on silica gel with an eluent of CH₃OH:CHCl₃ (3:97) to give the final product (0.25 g) as a pale yellow oil; TLC, $R_f$=0.5, silica gel, $CH_3OH:CHCl_3$ (3:97).

i. (Formula Ib, 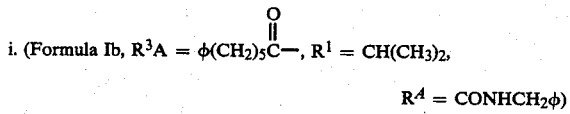

$R^4 = CONHCH_2\phi$)

A solution of a portion of the product of Example 2h (0.15 g, 0.27 mmol), DMSO (2.0 ml) and acetic anhydride (2.0 ml) was stirred overnight at room temperature. Ice water (30 ml) was added and the solution was stirred an additional hour. Ethyl acetate (50 ml) was added and the organic layer was collected, washed with a saturated aqueous solution of $NaHCO_3$ and brine. The ethyl acetate solution was dried with $Na_2SO_4$, filtered, and the solvent removed under reduced pressure to give a crude product (0.12 g). The product was purified by flash chromatography on silica gel to give the final product as an oil (0.05 g); TLC, $R_f$=0.66, silica gel, EtOAc:hexane (2:1); $^1H$ NMR (DMSO-$d_6$): 0.83 (m, 6H); 1.2–2.2 (m, 13H); 2.5 (m, 2H); 3.4 (m, 2H); 4.0–4.5 (m, 3H); 4.75 (m, 1H); 7.2 (m, 10H); 8.3–8.55 (m, 1H); 9.7 (m, 1H).

EXAMPLE 3

N-[(Phenylmethoxy)carbonyl]-L-valyl-N-[3,3-difluoro-1-(1-methylethyl-2,4-dioxo-4-[(phenylmethyl)amino]-butyl]-L-prolinamide (Formula Ic, 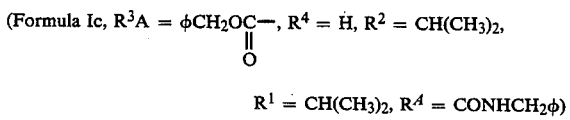

$R^1 = CH(CH_3)_2$, $R^4 = CONHCH_2\phi$)

a. N-Benzyloxycarbonyl-L-valyl-L-proline t-butyl ester

A solution of N-benzyloxycarbonyl-L-valine (56.25 g, 0.244 mol) and HOBT (60.67 g, 0.45 mol) in DMF (565 ml) was cooled to 5° C. DCC (50.89 g, 0.247 mol) was added to one portion. The mixture was stirred an additional 15 min at 5° C. and then L-proline t-butyl ester (38.36 g, 0.224 mol) was added. The mixture was stirred for an additional 2 hr at 5° C. and then for 48 hr at room temperature. The mixture was filtered and concentrated under vacuum. The oily residue was dissolved in EtOAc (1 liter) and washed successively with 20% aqueous citric acid, saturated aqueous $NaHCO_3$ and brine. The organic phase was dried over $Na_2SO_4$, filtered and concentrated under vacuum to afford the product (92 g) as a white foam; TLC, $R_f$=0.9, silica gel, $CHCl_3:EtOAc$ (85:15).

b. N—Benzyloxycarbonyl-L-valyl-L-proline (Formula XVIIc,

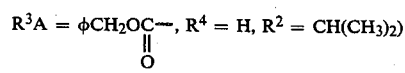

Trifluoroacetic acid (70 ml, 0.90 mol) was added to a solution of a portion of the product of Example 3a (16.5 g, 39.2 mmol) in $CH_2Cl_2$ (100 ml) at room temperature and the resulting mixture was stirred for 3 hr. The solution was diluted with toluene (100 ml) and concentrated under vacuum. The residue was taken up in toluene and reconcentrated 5 times to give the product (12.85 g) as a tan solid; TLC, $R_f$=0.45, silica gel, $MeOH:CH_2Cl_2$ (5:95).

c. N—Benzyloxycarbonyl-L-valyl-L-prolyl-L-valinal diethylacetal (Formula XVc, 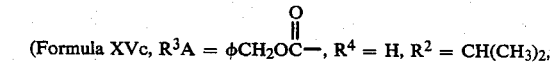

HOBT (4.21 g, 31.1 mmol) was added to a solution of a portion of the product of Example 3b (5.17 g, 15.55 mmol) and L-valinal diethylacetal (obtained as described in Example 1d) (2.73 g, 15.55 mmol) in dry THF (75 ml) at 0° C. under a nitrogen atmosphere. This solution was stirred for 15 min and 1-(3-dimethylaminopropyl)-3-ethyl carbodiimide hydrochloride (3.28 g, 17.1 mmol) followed by N-methylmorpholine (2.36 g, 23.3 mmol) were added. The mixture was stirred for 1 hr at 0° C. and for 3 days at room temperature. The reaction mixture was concentrated in vacuo and the residue was partitioned between EtOAc and $H_2O$. The organic layer was isolated and washed sequentially with aqueous 1N HCl, brine, saturated aqueous $NaHCO_3$ and brine, then dried over $MgSO_4$, filtered and concentrated to give a viscous oil. The product was purified by flash chromatography on silica gel with $CH_2Cl_2:Et_2O$:-MeOH (75:25:0.5) to give a colorless oil (4.4 g); TLC, $R_f$=0.55, silica gel, $CH_2Cl_2:Et_2O:MeOH$ (75:25:1).

d. L-Valyl-L-prolyl-L-valinal diethylacetal (Formula XVIIIc, $R^4$=H, $R^2$=$CH(CH_3)_2$, $R^1$=$CH(CH_3)_2$)

A portion of the product of Example 3c (3.63 g, 7.18 mmol) and 10% Pd/C (0.5 g) in EtOH (75 ml) was hydrogenated on a Parr shaker (3 atm $H_2$). When the theoretical amount of $H_2$ was consumed the mixture was filtered through diatomaceous earth and concentrated under vacuum to give the product (2.5 g); TLC, $R_f$=0.3, silica gel, $MeOH:CH_2Cl_2$ (1:9).

e. N—Benzyloxycarbonyl-L-valyl-L-prolyl-L-valinal (Formula VIc, 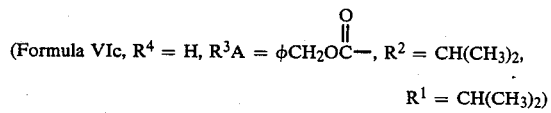

A mixture of p-toluenesulfonic acid (150 mg) and a portion of the product of Example 3c (500 mg, 0.988 mmol) in acetone (70 ml) was stirred at room temperature for 3 hr. The mixture was concentrated under vacuum and the residue was dissolved in EtOAc. This solution was washed with 5% aqueous $NaHCO_3$ and brine, dried over $MgSO_4$, filtered and concentrated to give a glass (410 mg); TLC, $R_f$=0.60, silica gel, $CH_2Cl_2:MeOH$ (95:5).

f. 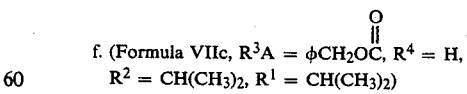

A product made using the method of Example 3e (0.62 g, 1.5 mmol), Zn dust (0.13 g), ethyl 2-bromo-2,2-difluoroacetate (0.336 g, 1.65 mmol), and THF (9.0 ml) were refluxed for ½ hr. An additional portion of Zn dust (0.13 g) and ethyl 2-bromo-2,2-difluoroacetate (0.33 g, 1.65 mmol) was added and allowed to reflux for an additional hour. The solution was cooled to room temperature and ethyl acetate (70 ml) was added. The resulting solution was washed with 1M KHSO₄ and brine and the organic layer was collected, dried with Na₂SO₄, filtered, and the solvent removed under reduced pressure to give a crude product which was purified by flash chromatography on silica gel with an eluent of hexane:ethyl acetate (30:70) to give the final product (0.66 g) as an oil; TLC, R_f=0.7, silica gel, hexane:ethyl acetate (30:70).

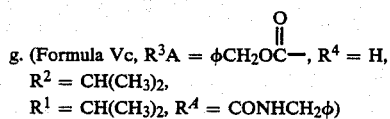

g. (Formula Vc, R³A = φCH₂OC—, R⁴ = H,
R² = CH(CH₃)₂,
R¹ = CH(CH₃)₂, R⁴ = CONHCH₂φ)

A portion of the product from Example 3f (0.41 g, 0.74 mmol), benzylamine (0.16 ml, 1.48 mmol) and ethanol (5 ml) were stirred at 65° C. for 5 hr. The resulting solution was cooled to room temperature and the solvent was removed under reduced pressure to give a crude product. The product was purified by flash chromatography to give the final product (0.3 g) as a clear oil; TLC, R_f=0.6, silica gel, hexane:ethyl acetate (30:70).

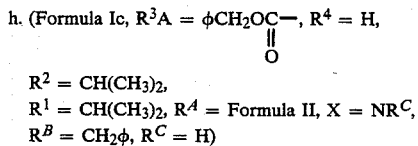

h. (Formula Ic, R³A = φCH₂OC—, R⁴ = H,
R² = CH(CH₃)₂,
R¹ = CH(CH₃)₂, R⁴ = Formula II, X = NR^C,
R^B = CH₂φ, R^C = H)

The product of Example 3g (0.30 g, 0.46 mmol), DMSO (4.0 ml) and acetic anhydride (4.0 ml) were stirred together at room temperature under N₂ for 24 hr. Ice water (80 ml) was added and the resulting solution stirred for 3 hr. Ethyl acetate (100 ml) was added and the organic layer was collected and washed with a saturated solution of aqueous NaHCO₃. The organic layer was collected, dried with Na₂SO₄, filtered and the solvent removed under reduced pressure to give a crude product (0.26 g). The product was purified by flash chromatography on silica gel to give the final product (0.2 g) as a white foam; TLC, R_f=0.5, silica gel, ethyl acetate:hexane (50:50).

Analysis calculated for C₃₂O₆N₄H₄₀F₂·½H₂O: C, 61.62; H, 6.62; N, 8.98. Found: C, 61.88, 61.57; H, 6.65, 6.46; N, 8.64, 8.73.

EXAMPLE 4

2-[[[3,3-Difluoro-1-(1-methylethyl)-2,4-dioxo-4-[(2-phenylethyl)amino]butyl]amino]carbonyl]-1-pyrrolidinecarboxylic acid phenylmethyl ester R⁴ = Formula II, X = NR^C, R^B = CH₂CH₂φ, R^C = H,
R³A = φCH₂OC—,
‖
O
R¹ = CH(CH₃)₂)

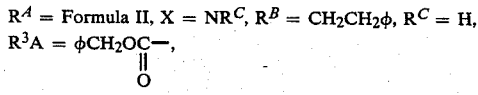

a. (Formula VIb, R¹ = CH(CH₃)₂, R³A = φCH₂OC—)

A solution of product obtained using the method of Example 2c (24 g, 60 mmol), p-toluene sulfonic acid (2.4 g) and acetone (1600 ml) was stirred at room temperature for 5 hr. The acetone was removed under water aspirator vacuum to leave an oily residue. The oily residue was taken up in chloroform and the chloroform solution was washed with saturated NaHCO₃, then brine and dried over MgSO₄. The MgSO₄ was filtered off and the filtrate was concentrated under vacuum to give the product (17.67 g, 91% yield) as an amber oil; TLC, R_f=0.46, silica gel, CHCl₃:MeOH (95:5).

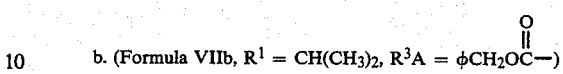

b. (Formula VIIb, R¹ = CH(CH₃)₂, R³A = φCH₂OC—)

A mixture of a portion of the product obtained using the method of Example 4a (2.5 g, 7.75 mmol), ethyl 2-bromo-2,2-difluoroacetate (1.57 g, 7.75 mmol), activated zinc (0.505 g, 7.75 mmol), and dry THF (125 ml) was heated at gentle reflux under nitrogen for 1 hr. The mixture was then allowed to cool to just below reflux and additional ethyl 2-bromo-2,2difluoroacetate (1.57 g, 7.75 mmol) and activated zinc (0.505 g, 7.75 mmol) were added. The reaction mixture was again heated to gentle reflux and was kept at reflux for 3 hr. The mixture was cooled and ethyl acetate (400 ml) was added. The ethyl acetate solution was washed with 1M KHSO₄ solution and brine and was dried over MgSO₄. The MgSO₄ was filtered off and the filtrate was concentrated under water aspirator vacuum to give a crude product (3.7 g). The product was purified by flash chromatography (EtOAc/hexane, 1:1, silica) to give 1.53 g (45% yield) of the desired product as a light yellow waxy solid; TLC, R_f=0.45, silica gel, petroleum ether EtOAc (33:66).

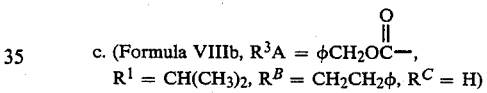

c. (Formula VIIIb, R³A = φCH₂OC—,
R¹ = CH(CH₃)₂, R^B = CH₂CH₂φ, R^C = H)

A mixture of a portion of the product from Example 4b (0.5 g, 1.09 mmol), 2-phenethylamine (0.26 g, 2.18 mmol) and absolute ethanol (20 ml) was heated at gentle reflux, with stirring, under N₂ for 4 hr. The mixture was then allowed to cool to room temperature and was stirred overnight at room temperature. The mixture was concentrated under vacuum and the resulting residue was dissolved in CH₂Cl₂. The CH₂Cl₂ solution was washed with 1N HCl and brine, dried over MgSO₄, filtered, and the filtrate concentrated under vacuum to afford, after purification by flash chromatography (CHCl₃:MeOH (98:2)), the product (0.35 g, 60%) as a white solid; TLC, R_f=0.2, silica gel, CHCl₃:CH₃OH (95:5).

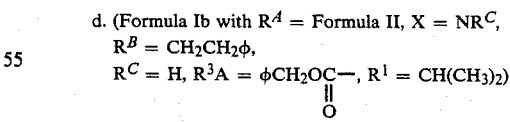

d. (Formula Ib with R⁴ = Formula II, X = NR^C,
R^B = CH₂CH₂φ,
R^C = H, R³A = φCH₂OC—, R¹ = CH(CH₃)₂)

A solution of Dess-Martin periodinane (2.42 g, 5.72 mmol) and dry CH₂Cl₂ (5 ml) was added to a stirred solution of the product from Example 4c (0.3 g, 0.57 mmol) and dry CH₂Cl₂ (20 ml) at room temperature under N₂. TFA (0.65 g, 5.72 mmol) was added and the resulting mixture was stirred at room temperature overnight. Ethyl acetate (25 ml) was added to the reaction mixture and the mixture was extracted with saturated Na₂S₂O₃, saturated NaHCO₃, and brine, dried over MgSO₄, filtered and the filtrate concentrated under vacuum to afford, after purification by flash chromatography (MeOH:CHCl$_3$ (3.97)), the product (0.1 g, 33%); TLC, R$_f$=0.74, silica gel, CHCl$_3$:CH$_3$OH (95:5).

Analysis calculated for C$_{28}$H$_{33}$F$_2$N$_3$O$_6$.1.5H$_2$O: C, 60.42; H, 6.50; N, 7.55. Found: C, 60.46; H, 6.00; N, 7.54.

EXAMPLE 5

2-[[[3,3-Difluoro-1-(1-methylethyl)2,4-dioxo-4-[(phenylmethyl)amino]butyl]amino]carbonyl]-1-pyrrolidinecarboxylic acid phenylmethyl ester (Formula Ib with R$^A$ = Formula II, X = NR$^C$,
R$^B$ = CH$_2$φ, R$^C$ = H, R$^1$ = CH(CH$_3$)$_2$,
R$^3$A = φCH$_2$OC—)
‖
O a. (Formula VIIIb, R$^3$A = φCH$_2$OC—,
R$^1$ = CH(CH$_3$)$_2$, R$^B$ = CH$_2$φ, R$^C$ = H)

Using the method of Example 4c, product prepared using method 4b was allowed to react with benzylamine to provide the crude product which was purified by flash chromatography on silica gel with an eluant of MeOH:CHCl$_3$ (2:98) to give the title product (53%); TLC, R$_f$=0.66, silica gel, MeOH:CHCl$_3$ (5:95).

b. (Formula Ib with R$^A$ = Formula II,
X = NR$^C$, R$^B$ = CH$_2$φ,
R$^C$ = H, R$^1$ = CH(CH$_3$)$_2$, R$^3$A = φCH$_2$O—C—)
‖
O Using the method of Example 4d, the product of Example 5a was oxidized to afford, after purification by flash chromatography (MeOH:CHCl$_3$ (2:98)), the title product (38%); TLC, R$_f$=0.68, silica gel, MeOH:CHCl$_3$ (5:95).

Analysis calculated for C$_{27}$H$_{31}$F$_2$N$_3$O$_5$: C, 62.90; H, 6.06; N, 8.15. Found: C, 62.71; H, 6.15; N, 7.98.

EXAMPLE 6

2-[[[3,3-Difluoro-1-(methylethyl)-2,4-dioxo-4-[[(1-tricyclo[3.3.1.1$^{3,7}$]decyl)methyl]amino]butyl]amino]carbonyl]-1-pyrrolidinecarboxylic acid phenylmethyl ester (Formula Ib with R$^A$ = Formula II, X = NR$^C$,
R$^B$ = CH$_2$—adamantyl, R$^C$ = H,
R$^1$ = CH(CH$_3$)$_2$, R$^3$A = φCH$_2$OC—)
‖
O a. (Formula XXVIb, R$^3$A = φCH$_2$OC—,
‖
O
R$^1$ = CH(CH$_3$)$_2$)

A solution of product prepared using the method of Example 4b (3.0 g, 6.57 mmol) and dry CH$_2$Cl$_2$ (10 ml) was added to a stirred mixture of Dess-Martin periodinane (13.92 g, 32.85 mmol) and dry CH$_2$Cl$_2$ (140 ml) at room temperature under N$_2$. The mixture was stirred at room temperature overnight. Ethyl acetate (200 ml) was added to the reaction mixture and the resulting mixture was extracted with saturated Na$_2$S$_2$O$_3$, saturated NaHCO$_3$, brine, then dried over MgSO$_4$, filtered and the filtrate concentrated under vacuum to afford the product (2.96 g, 98% yield); TLC, R$_f$=0.8, silica gel, CHCl$_3$:CH$_3$OH (95:5).

b. (Formula XXVIIb, R$^3$A = φCH$_2$OC—,
‖
O
R$^1$ = CH(CH$_3$)$_2$)

A 1N sodium hydroxide solution (0.55 g, 0.55 mmol) was added to a stirred solution of a portion of the product from Example 6a (1.0 g, 2.19 mmol) and methanol (3 ml) at room temperature. The resulting solution was stirred at room temperature for 3 hr, then treated with water (20 ml), and the resulting solution was extracted with EtOAc. The aqueous layer was made acidic (pH 2) with 1N HCl and then extracted with ethyl acetate. The ethyl acetate layer was washed with brine and dried (MgSO$_4$). The MgSO$_4$ was filtered off and the filtrate was concentrated under vacuum to leave an oily residue which was dried under high vacuum to give the product (0.17 g, 91%); TLC, R$_f$=0.15, silica gel, CHCl$_3$:MeOH:HOAc (95:5:0.5).

c. (Formula Ib with R$^A$ = Formula II, X = NR$^C$,
R$^B$ = CH$_2$—adamantyl, R$^C$ = H,
R$^3$A = φCH$_2$OC—, R$^1$ = CH(CH$_3$)$_2$)
‖
O WSCDI (0.123 g, 0.645 mmol) was added to a stirred solution of product prepared according to the method of Example 6b (0.25 g, 0.586 mmol), 1-adamantanemethylamine (0.586 mmol), HOBT (87 mg, 0.645 mmol) and dry THF (10 ml) under N$_2$ at room temperature. The mixture was stirred at room temperature overnight. The THF was removed under vacuum, the residue dissolved in ethyl acetate and the ethyl acetate solution washed successively with 1N HCl, saturated NaHCO$_3$ and brine. The organic solution was dried over MgSO$_4$, filtered and the filtrate concentrated under vacuum to afford a crude product (0.49 g). Purification by flash chromatography (CHCl$_3$) afforded the final product (0.21 g, 63%); TLC, R$_f$=0.52, silica gel, CHCl$_3$:CH$_3$OH (99:1).

Analysis calculated for C$_{31}$H$_{41}$F$_2$N$_3$O$_5$0.25H$_2$O: C, 64.39; H, 7.23; N, 7.26. Found: C, 64.20; H, 7.22; N, 7.20.

EXAMPLE 7

2-[[[3,3-Difluoro-1-(1-methylethyl)-4-[[4-(1-methylethyl)phenyl]amino]-2,4-dioxobutyl]amino]carbonyl]-1-pyrrolidinecarboxylic acid phenylmethyl ester (Formula Ib with R$^A$ = Formula II, X = NR$^C$,
R$^B$ = 4-[CH(CH$_3$)$_2$]φ, R$^C$ = H, R$^3$A = φCH$_2$OC—,
‖
O
R$^1$ = CH(CH$_3$)$_2$)

Using the method of Example 6c, a product prepared according to Example 6b was allowed to react with 4-isopropylaniline to afford, after purification by flash chromatography (MeOH:CHCl$_3$ (2:98)), the product (48%); TLC, R$_f$=0.48, silica gel, MeOH:CHCl$_3$ (2:98).

Analysis calculated for C$_{29}$H$_{35}$F$_2$N$_3$O$_5$.0.25H$_2$O: C, 63.54; H, 6.53; N, 7.66. Found: C, 63.41; H, 6.49; N, 7.57.

EXAMPLE 8

N-[4-(Methoxycarbonyl)benzoyl]-beta-alanyl-N-[3,3-difluoro-1-(1-methylethyl)-2,4-dioxo-4-[(2,phenylethyl)amino]butyl]-L-prolinamide (Formula Ib with $R^A$ = Formula II, $X = NR^C$, $R^B = CH_2CH_2\phi$, $R^C = H$,

$R^3A = [4\text{-}(CH_3O\text{---}C)\phi]CNH(CH_2)_2C\text{---}$, $R^1 = CH(CH_3)_2)$ a. (Formula XIb, $R^B = CH_2CH_2\phi$, $R^C = H$, $R^1 = CH(CH_3)_2$)

A mixture of product prepared according to the method of Example 4c, ethanol (100 ml), and 10% Pd/C (0.2 g) was placed under a hydrogen atmosphere (1 atmosphere) for 2 hr. The reaction mixture was filtered through diatomaceous earth, washing with ethanol. The filtrate was concentrated under vacuum to give the product (0.64 g, 96%); TLC, $R_5=0.05$, silica gel, $CHCl_3:MeOH$ (95:5).

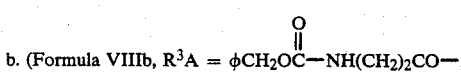
b. (Formula VIIIb, $R^3A = \phi CH_2OC\text{---}NH(CH_2)_2CO\text{---}$, $R^B = CH_2CH_2\phi$, $R^C = H$, $R^1 = CH(CH_3)_2$ Using the method of Example 6c, the product of Example 8a was allowed to react with N-carbobenzeneoxy-beta-alanine (CBZ-beta-alanine) to afford, after purification by flash chromatography (MeOH:CHCl3 (3:97)), the product (68.9%); TLC, $R_f=0.40$, silica gel, $CHCl_3:MeOH$ (95:5).

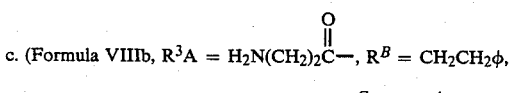
c. (Formula VIIIb, $R^3A = H_2N(CH_2)_2C\text{---}$, $R^B = CH_2CH_2\phi$, $R^C = H$, $R^1 = CH(CH_3)_2$)

A mixture of the product from Example 8b, ethanol (25 ml) and 10% Pd/C (0.1 g) was stirred at room temperature under a hydrogen atmosphere at about $1.013 \times 10^5$ Pascals guage (15 psig) overnight. The mixture was filtered through diatomaceous earth and the diatomaceous earth was washed with ethanol. The combined filtrates were concentrated under vacuum to give the product (0.32 g, 82%); m/e=469; $^1H$ NMR (DMSO-$d_6$), 0.84 (m, 6H); 1.98-2.5 (m, 9H); 2.74 (m, 4H); 3.3 (m, 4H); 4.2 (m, 2H); 6.0 (m, 1H); 7.23 (m, 5H); 7.5, (m, 1H); 8.74 (m, 1H).

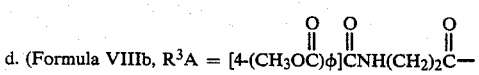
d. (Formula VIIIb, $R^3A = [4\text{-}(CH_3OC)\phi]CNH(CH_2)_2C\text{---}$ $R^B = CH_2CH_2\phi$, $R^C = H$, $R^1 = CH(CH_3)_2$)

WSCDI (0.114 g, 0.59 mmol) was added to a stirred solution of 1,4-benzenedicarboxylic acid monomethyl ester (prepared as described in Example 11a) (97.4 mg, 0.54 mmol), the product from 8c (0.254 g, 0.54 mmol), HOBT (0.146 g, 1.08 mmol) and dry THF (20 ml) at 0° C. under nitrogen. The reaction mixture was stirred at 0° C. for 1 hr; it was then allowed to come to room temperature and was stirred at room temperature overnight. The THF was removed under vacuum. The residue was dissolved in ethyl acetate. The solution was washed successively with 1N HCl, saturated NaHCO3 and brine, and was then dried over MgSO4, filtered and the filtrate concentrated under vacuum to afford, after purification by column chromatography ($CHCl_3$:MeOH (97:3)), the product (0.219 g, 64%); TLC, $R_f=0.42$, silica gel, $CHCl_3:CH_3OH$ (95:5).

e. (Formula Ib with $R^A$ = Formula II, $X = NR^C$, $R^B = CH_2CH_2\phi$, $R^C = H$,

$R^3A = [4\text{-}(CH_3O\text{---}C)\phi]CNH(CH_2)_2C\text{---}$, $R^1 = CH(CH_3)_2)$ Using the method of Example 6a, but using 10 equivalents of the Dess-Martin periodinane reagent, the product of Example 8d was oxidized to afford, after purification by flash chromatography ($CHCl_3$:MeOH (97:3)), the product (77%); TLC, $R_f=0.46$, silica gel, $CHCl_3:MeOH$ (95:5).

Analysis calculated for $C_{32}H_{38}F_2N_4O_7.2H_2O$: C, 57.82; H, 6.30; N, 8.42. Found: C, 57.90; H, 5.86; N, 8.36.

EXAMPLE 9

N-(4-Carboxybenzoyl)-beta-alanyl-N-[3,3-dilfuoro-1-(1-methylethyl)-2,4-dioxo-4-[(2-phenylethyl)amino]butyl]-L-prolinamide (Formula Ib with $R^A$ = Formula II, $X = NR^C$, $R^B = CH_2CH_2\phi$, $R^C = H$,

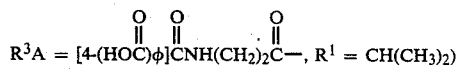
$R^3A = [4\text{-}(HOC)\phi]CNH(CH_2)_2C\text{---}$, $R^1 = CH(CH_3)_2)$ A solution of the product of Example 8e (0.105 g, 0.167 mmol), $CH_3OH$ (1.0 ml), $H_2O$ (1.0 ml) and 1N NaOH (0.33 ml) was stirred at room temperature for 3 hr. Water (3.0 ml) was added and the mixture was extracted with EtOAc. The aqueous layer was taken to pH 2.0 with 1N HCl and extracted with EtOAc. The EtOAc layer was dried (MgSO4), filtered and concentrated under vacuum to give the product (0.080 g, 78.8%); TLC, $R_f=0.33$, silica gel, MeOH:CHCl3:HOAc (95:5:0.5).

Analysis calculated for $C_{30}H_{34}N_4O_7F_2.0.75H_2O$: C, 59.27; H, 6.02; N, 8.91. Found: C, 59.18; H, 5.96; N, 8.63.

EXAMPLE 10

N-[(phenylmethoxy)carbonyl]-L-valyl-N-[3,3-dilfuoro-1-(1-methylethyl)-2,4-dioxo-4-[(phenylmethyl)amino]butyl]-L-prolinamide (Formula Ic with $R^A$ = Formula II, $X = NR^C$,

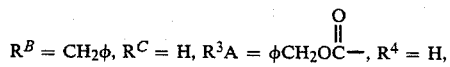
$R^B = CH_2\phi$, $R^C = H$, $R^3A = \phi CH_2OC\text{---}$, $R^4 = H$, $R^2 = CH(CH_3)_2$, $R^1 = CH(CH_3)_2)$ a. N-Benzyloxycarbonyl-L-valyl-L-proline t-butyl ester A solution of N-benzyloxycarbonyl-L-valine (56.25 g, 0.244 mol) and HOBT (60.67 g, 0.45 mol) in DMF (565 ml) was cooled to 5° C. DCC (50.89 g, 0.247 mol) was added in one portion. The mixture was stirred an additional 15 min at 5° C. and then L-proline t-butyl ester (38.36 g, 0.224 mol) was added. The mixture was stirred an additional 2 hr at 5° C. and then for 48 hr at room temperature. The mixture was filtered and concentrated under vacuum. The oily residue was dissolved in EtOAc (1 liter) and the solution was washed successively with 20% aqueous citric acid, saturated aqueous NaHCO$_3$ and brine. The organic phase was dried over Na$_2$SO$_4$, filtered and concentrated under vacuum to afford the product (92 g) as a white foam; TLC, R$_f$=0.9, silica gel, CHCl$_3$:EtOAc (85:15).

b. N—Benzyloxycarbonyl-L-valyl-L-proline (Formula

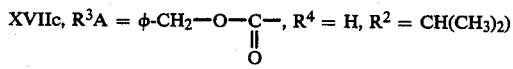
XVIIc, R$^3$A = φ-CH$_2$—O—C—, R$^4$ = H, R$^2$ = CH(CH$_3$)$_2$)

Trifluoroacetic acid (70 ml, 0.90 mol) was added to a solution of a portion of the product of Example 10a (16.5 g, 39.2 mmol) in CH$_2$Cl$_2$ (100 ml) at room temperature and the resulting mixture was stirred for 3 hr. The solution was diluted with toluene (100 ml) and concentrated under vacuum. The residue was taken up in toluene and reconcentrated 5 times to give the product (12.85 g) as a tan solid; TLC, R$_f$=0.45, silica gel, MeOH:CH$_2$Cl$_2$ (5:95).

c. L-Valinal diethylacetal (Formula XVIIIa, R$^1$=CH(CH$_3$)$_2$)

A mixture of the product of Example 1c (147.8 g, 0.478 mol) and 10% Pd/C (10 g) in EtOAc (1500 ml) was stirred under H$_2$ (1 atm.) until 2500 ml of H$_2$ were consumed. Twice during this time the reaction was interrupted and 10% Pd/C (10 g) was added. The reaction mixture was then filtered through a pad of diatomaceous earth. 10% Pd/C (10 g) was added and the reaction mixture was stirred until 10.92 liters of H$_2$ were consumed. The reaction mixture was filtered through diatomaceous earth and the filtrate was concentrated under vacuum to give the product (78.8 g) as a pale yellow oil; [alpha]$_D^{25}$=+7.8.

d. N—Benzyloxycarbonyl-L-valyl-L-prolyl-L-valinal

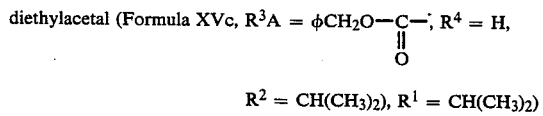
diethylacetal (Formula XVc, R$^3$A = φCH$_2$—O—C—, R$^4$ = H,
R$^2$ = CH(CH$_3$)$_2$), R$^1$ = CH(CH$_3$)$_2$)

HOBT (4.21 g, 31.1 mmol) was added to a solution of the product of Example 10b (5.17 g, 15.55 mmol) and the product of Example 10c (2.73 g, 15.55 mmol) in dry THF (75 ml) at 0° C. under a nitrogen atmosphere. This solution was stirred for 15 min and 1-(3-dimethylaminopropyl)-3-ethyl carbodiimide hydrochloride (3.28 g, 17.1 mmol) followed by N-methylmorpholine (2.36 g, 23.3 mmol) were added. The mixture was stirred for 1 hr at 0° C. and for 3 days at room temperature. The reaction mixture was concentrated under vacuum and the residue was partitioned between EtOAc and H$_2$O. The organic layer was isolated and sequentially washed with aqueous 1N HCl, brine, saturated aqueous NaHCO$_3$ and brine, then dried over MgSO$_4$, filtered and concentrated to give a viscous oil. The product was purified by flash chromatography on silica gel with CH$_2$Cl$_2$:Et$_2$O:MeOH (75:25:0.5) to give a colorless oil (4.4 g); TLC, R$_f$=0.55, silica gel, CH$_2$Cl$_2$:Et$_2$O:MeOH (75:25:1).

e. L-Valyl-L-prolyl-L-valinal diethylacetal (Formula VIIIc, R$^4$=H, R$^2$=CH(CH$_3$)$_2$, R$^1$=CH(CH$_3$)$_2$)

A mixture of the product of Example 10d (3.63 g, 7.18 mmol), 10% Pd/C (0.5 g), and EtOH (75 ml) was hydrogenated using a Parr shaker (3 atm H$_2$). When the theoretical amount of H$_2$ was consumed the mixture was removed from the Paar shaker, filtered through diatomaceous earth and concentrated under vacuum to give the product (2.5 g); TLC, R$_f$=0.3, silica gel, MeOH:CH$_2$Cl$_2$ (1:9).

f. N-Benzyloxycarbonyl-L-valyl-L-prolyl-L-valinal

A mixture of p-toluenesulfonic acid (150 mg) and a portion of the product of Example 10d (500 mg, 0.988 mmol) in acetone (70 ml) was stirred at room temperature for 3 hr. The mixture was concentrated under vacuum and the residue was dissolved in EtOAc. The EtOAc solution was washed with 5% aqueous NaHCO$_3$ and brine, dried over MgSO$_4$, filtered and concentrated to give the product as a glass (0.410 g); TLC, R$_f$=0.60, silica gel, CH$_2$Cl$_2$:MeOH (95:5).

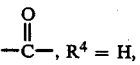
g. (Formula VIIc, R$^3$A = φCH$_2$O—C—, R$^4$ = H,
R$^2$ = CH(CH$_3$)$_2$, R$^1$ = CH(CH$_3$)$_2$)

The product of Example 10f (0.62 g, 1.5 mmol), Zn dust (0.13 g), ethyl 2-bromo-2,2-difluoroacetate (0.336 g, 1.65 mmol) and THF (9.0 ml) were refluxed for 30 min under N$_2$. Additional portions of Zn dust (0.13 g) and ethyl 2-bromo-2,2-difluoroacetate (0.33 g, 1.65 mmol) were added and the mixture allowed to reflux for an additional hour. The solution was cooled to room temperature and ethyl acetate (70 ml) was added. The resulting mixture was washed with 1M KHSO$_4$ and brine and the organic layer was collected, dried with Na$_2$SO$_4$, filtered, and the solvent removed under reduced pressure to give a crude product. The product was purified by flash chromatography on silica gel with an eluent of hexane:ethyl acetate (30:70) to give the final product (0.66 g) as an oil; TLC, R$_f$=0.7, silica gel, hexane:ethyl acetate (30:70).

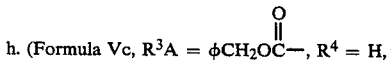
h. (Formula Vc, R$^3$A = φCH$_2$OC—, R$^4$ = H,
R$^2$ = CH(CH$_3$)$_2$, R$^1$ = CH(CH$_3$)$_2$, R$^4$ = CONHCH$_2$φ)

A portion of the product from Example 10g (0.41 g, 0.74 mmol), benzylamine (0.16 ml, 1.48 mmol) and ethanol (5 ml) were stirred at 65° C. for 5 hr. The resulting solution was cooled to room temperature and the solvent was removed under reduced pressure to give a crude product. The product was purified by flash chromatography on silica gel to give the final product (0.3 g); TLC, R$_f$=0.6, silica gel, hexane:ethyl acetate (30:70).

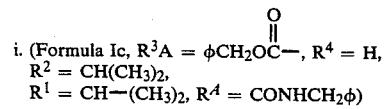
i. (Formula Ic, R$^3$A = φCH$_2$OC—, R$^4$ = H,
R$^2$ = CH(CH$_3$)$_2$,
R$^1$ = CH—(CH$_3$)$_2$, R$^4$ = CONHCH$_2$φ)

The product of Example 10h (0.30 g, 0.46 mmol), DMSO (4.0 ml) and acetic anhydride (4.0 ml) were stirred together at room temperature under N$_2$ for 24 hr.

Ice water (80 ml) was added and the resulting solution stirred for 3 hr. Ethyl acetate (100 ml) was added and the organic layer was collected and washed with a saturated solution of aqueous NaHCO$_3$. The organic layer was collected, dried with Na$_2$SO$_4$, filtered and the solvent removed under reduced pressure to give a crude product (0.26 g). The product was purified by flash chromatography on silica gel to give the final product (0.2 g) as a white foam; TLC, R$_f$=0.5, silica gel, ethyl acetate:hexane (50:50).

Analysis calculated for C$_{32}$O$_6$N$_4$H$_{40}$F$_2$·½H$_2$O: C, 61.62; H, 6.62; N, 8.98. Found: C, 61.72; H, 6.49; N, 8.68.

EXAMPLE 11

N-[4-(Methoxycarbonyl)benzoyl]-L-valyl-N-[3,3-difluoro-1-(1-methylethyl)-2,4-dioxo-4-](2-phenylethyl)amino]butyl]-L-prolinamide (Formula Ic with R$^A$ = Formula II, X = NR$^C$,
R$^B$ = CH$_2$CH$_2\phi$, R$^C$ = H, R$^1$ = CH(CH$_3$)$_2$,
R$^2$ = CH(CH$_3$)$_2$, R$^4$ = H, R$^3$A = [4-(CH$_3$OC)$\phi$]C—)
  ‖   ‖
  O   O a. 4-Methoxycarbonylbenzenecarboxylic acid or 1,4-benzenedicarboxylic acid monomethyl ester Concentrated sulfuric acid (277.5 ml, 5.2 mol) was added dropwise over ½ hr to a stirred solution of chromium (VI) oxide (299.25 g, 2.99 mol) and water (925 ml) at 0°. The resulting solution was added dropwise over 1 hr to a stirred solution of methyl-4-(hydroxymethyl)-benzoate (92.5 g, 0.564 mol) and acetone (4.6 l) at 0°. The reaction mixture was allowed to warm to room temperature and stirred overnight. The supernatant was decanted before the black tar-like residue was extracted with acetone. The decanted supernatant and acetone extracts were combined and concentrated under vacuum to leave a dark brown residue which was triturated with cold water (4 liters). The precipitate which formed was collected, washed three times with water (1 liter), and dried to give 94.6 g (94%) of the title compound as white crystals, m.p. 218°–221° C.

b. (Formula XVc, R$^1$ = CH(CH$_3$)$_2$, R$^2$ = CH(CH$_3$)$_2$,
R$^4$ = H, R$^3$A = [4-(CH$_3$OC)$\phi$]C—)
  ‖   ‖
  O   O Using the method of Example 6c, a product prepared according to Example 11a was allowed to react with the product prepared according to Example 3d to afford the final product (83%); TLC, R$_f$=0.45, silica gel, CHCl$_3$:MeOH (95:5).

c. (Formula VIc, R$^1$ = CH(CH$_3$)$_2$, R$^2$ = CH(CH$_3$)$_2$,
R$^4$ = H, R$^3$A = [4-(CH$_3$OC)$\phi$]C—)
  ‖   ‖
  O   O Using the method of Example 4a, a product prepared according to the method of Example 11b was converted to the final product (94%); TLC, R$_f$=0.29, silica gel, CHCl$_3$:MeOH (95:5).

d. (Formula VIIc, R$^1$ = CH(CH$_3$)$_2$, R$^2$ = CH(CH$_3$)$_2$,
R$^4$ = H, R$^3$A = CH$_3$OC—)
  ‖
  O Using the method of Example 4b, the product prepared according to Example 11c was converted to the final product (23%); TLC, R$_f$=0.58, silica gel, CHCl$_3$:MeOH (95:5).

e. (Formula Vc with R$^A$ = Formula II, X = NR$^C$,
R$^B$ = CH$_2$CH$_2\phi$, R$^C$ = H, R$^1$ = CH(CH$_3$)$_2$,
R$^2$ = CH(CH$_3$)$_2$, R$^4$ = H, R$^3$A = [4(CH$_3$OC)$\phi$]C—)
  ‖   ‖
  O   O Using the method of Example 4c, the product of Example 11d was allowed to react with 2-phenethylamine to give the final product (64%); TLC, R$_f$=0.52, silica gel, CHCl$_3$:MeOH (95:5).

f. (Formula Ic with R$^A$ = Formula II, X = NR$^C$,
R$^B$ = CH$_2$CH$_2\phi$, R$^C$ = H, R$^1$ = CH(CH$_3$)$_2$,
R$^2$ = CH(CH$_3$)$_2$, R$^4$ = H, R$^3$[4-(CH$_3$OC)$\phi$]C—)
  ‖   ‖
  O   O Using the method of Example 4d, the product prepared according to Example 11e was converted to the final product (66%); TLC, R$_f$=0.6, CHCl$_3$:MeOH (95:5).

Analysis calculated for C$_{34}$H$_{42}$F$_2$N$_4$O$_7$·0.5 H$_2$O: C, 61.34; H, 6.51; N, 8.41. Found: C, 61.48; H, 6.39; N, 8.06.

EXAMPLE 12

N-(4-Carboxybenzoyl)-L-valyl-N-[3,3-difluoro-1-(1-methylethyl)-2,4-dioxo-4-[(2-phenylethyl)amino]butyl]-L-prolinamide (Formula Ic, R$^3$A = [4(HOC)$\phi$]C—, R$^A$ = Formula II,
  ‖   ‖
  O   O
X = NR$^C$, R$^B$ = CH$_2$CH$_2\phi$, R$^C$ = H,
R$^1$ = CH(CH$_3$)$_2$, R$^2$ = CH(CH$_3$)$_2$, R$^4$ = H)

Water (1.5 ml) was added to a stirred solution of a product made using the procedure of Example 11f (0.2 g, 0.3 mmol) and CH$_3$OH (2.0 ml) at room temperature. A solution of 1N NaOH (0.68 ml, 0.68 mmol) was added and the resulting solution was stirred for 5 hr at room temperature. Water (25 ml) was added and the aqueous solution was extracted with EtOAc. The aqueous layer was acidified with 1N NCl to pH 2 and the solution was extracted twice with EtOAc. The EtOAc extracts were combined and washed with 1N HCl and brine, dried over MgSO$_4$, filtered and concentrated under vacuum to give the product (0.141 g, 73%); TLC, R$_f$=0.52, silica gel, CHCl$_3$:MeOH:HOAc (95:5.0:0.5).

Analysis calculated for: C$_{33}$H$_{40}$F$_2$N$_4$O$_7$·H$_2$O: C, 59.99; H, 6.40; N, 8.48. Found: C, 60.09; H, 6.29; N, 8.13.

EXAMPLE 13

2-[[[3,3-Difluoro-5-methyl-1-(1-methylethyl)-2-oxohexyl]amino]carbonyl]-1-pyrrolidinecarboxylic acid phenylmethyl ester (Formula Ib, R$^A$ = CH$_2$CH(CH$_3$)$_2$, R$^1$ = CH(CH$_3$)$_2$,
R$^3$A = $\phi$CH$_2$OC—)
  ‖
  O a. (Formula XXV, R$^A$=CH$_2$CH(CH$_3$)$_2$, R$^x$=CH$_3$)
To a stirred solution of 4-methyl-2-oxopentanoic acid, sodium salt (24.81 g, 0.163 mol) in DMF/H$_2$O (3:1, 160 ml) was added methyl iodide (34.72 g, 0.245 mol). The reaction was stirred for 72 hr and H₂O (800 ml) was added. The aqueous solution was extracted with Et₂O. The combined extracts were washed with H₂O and brine, dried (Na₂SO₄), filtered and concentrated under vacuum to give a crude product. The product was purified by vacuum distillation (water aspirator) to give a pale yellow liquid (19.95 g); b.p. 58°-59°; $^1$H NMR (CDCl₃): 0.98 (d (J=6.5), 6H); 2.19 (m, 1H); 2.71 (d (J=6.4), 2H); 3.85 (s, 3H).

b. (Formula XXIV, R$^A$=CH₂CH(CH₃)₂, R$^x$=CH₃)

Diethylaminosulfur trifluoride (33.79 g, 0.210 mol) was added to a cooled (0° C.) solution of a product of Example 13a (19.95 g, 0.139 mol) in CH₂Cl₂ (125 ml). The reaction was allowed to warm to room temperature and stirred for 72 hr. The reaction was cautiously poured into ice water (1 liter), neutralized with solid NaHCO₃, and extracted with CH₂Cl₂. The combined extracts were washed with H₂O and brine, dried (MgSO₄), filtered and concentrated under vacuum to give a crude product. The product was purified by vacuum distillation (water aspirator) to give the final product (16.93 g) as a clear liquid; b.p. 39°-40°; $^1$H NMR (CDCl₃): 0.99 (d (J=6.3), 6H); 1.97 (m, 3H); 3.87 (s, 3H).

c. (Formula XX, R$^A$=CH₂CH(CH₃)₂)

Diisobutylaluminum hydride (1M solution in hexane, 7.2 ml, 7.2 mmol) was added slowly to a stirred, cooled (−78° C.) solution of a portion of the product of Example 13b (1.0 g, 6.0 mmol) in dry Et₂O (25 ml) under an atmosphere of dry N₂. The reaction was stirred for 2 hr at −78° C. and 1M aqueous H₂SO₄ (35 ml) was added. The resulting mixture was stirred for 10 min, the layers were separated and the aqueous layer was extracted with Et₂O. The combined extracts were washed with saturated aqueous NaHCO₃ and brine, dried (Na₂SO₂), filtered and concentrated under vacuum to give a crude product as a clear oil (1.03 g) which was used without further purification; $^1$H NMR (CDCl₃): 1.0 (d (J=6.4), 6H); 1.85 (m, 3H); 2.72 (d (J=10.45), 1H); 3.51 (s, 3H); 4.50 (m, 1H).

d. (Formula XXI, R$^1$=CH(CH₃)₂, R$^A$=CH₂CH(CH₃)₂)

Potassium carbonate (1.5 g, 0.011 mol) was added to a stirred mixture of nitroisobutane (0.87 g, 0.0085 mol) and a product of Example 13c (1.85 g, 0.011 mol) and the reaction was stirred overnight. H₂O (10 ml) was added and the mixture acidified with 1N aqueous HCl. The mixture was extracted with Et₂O and the combined extracts were washed with H₂O and brine, dried (Na₂SO₄), filtered and concentrated to give a crude product which was purified by flash chromatography on silica gel using CH₂Cl₂ as eluent to give the product (1.2 g); TLC, R$_f$=0.6, silica gel, CH₂Cl₂.

e. (Formula XXII, R$^1$=CH(CH₃)₂, R$^A$=CH₂CH(CH₃)₂)

A solution of a product of Example 13d (0.72 g, 3.44 mmol) in dry Et₂O (5 ml) was added dropwise to a stirred suspension of LiAlH₄ (0.39 g, 10.3 mmol) in dry Et₂O (10 ml) under an atmosphere of dry N₂. The reaction was stirred for 1 hr at room temperature and H₂O (1 ml) was cautiously added, followed by 20% aqueous sodium potassium tartrate (20 ml). The mixture was extracted with Et₂O. The combined extracts were washed with brine, dried (Na₂SO₄), filtered and concentrated to give the product (0.49 g) which was used without further purification; TLC, R$_f$=0.42, silica gel, CH₂Cl₂.

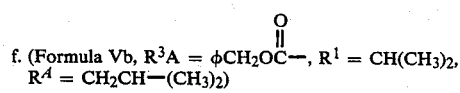
f. (Formula Vb, R$^{3A}$ = φCH₂OC—, R$^1$ = CH(CH₃)₂, R$^A$ = CH₂CH—(CH₃)₂)

Isobutyl chloroformate (0.097 ml, 0.75 mmol) was added to a precooled (−15° C.) solution under N₂ of CBZ-proline (0.185 g, 0.75 mmol), N-methylmorpholine (0.062 ml, 0.75 mmol), and THF (5.0 ml) and the mixture was allowed to stir for 0.5 hr at −15° C. The mixture was then cooled to −40° C. and a solution of a product of Example 13e and THF (2.0 ml) was added slowly. The resulting mixture was allowed to warm slowly to room temperature overnight. The mixture was filtered and the THF was removed under vacuum. EtOAc was added and the organic solution was sequentially extracted with 1N HCl, saturated NaHCO₃ and brine and then dried over Na₂SO₄, filtered and the EtOAc removed under vacuum, to afford the product; TLC, R$_f$=0.45, silica gel, MeOH:CHCl₃ (5:95).

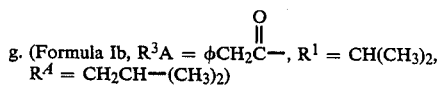
g. (Formula Ib, R$^{3A}$ = φCH₂C—, R$^1$ = CH(CH₃)₂, R$^A$ = CH₂CH—(CH₃)₂)

Using the method of Example 1g, a product of Example 13f was oxidized to afford, after purification by flash chromatography (MeOH:CHCl₃ (2:98)), the product (40%); TLC, R$_f$=0.75, silica gel, MeOH:CHCl₃ (5:95); $^1$H NMR (d₆-DMSO): 0.87 (m, 12H); 1.9 (m, 8H); 3.4 (m, 2H); 4.4 (m, 1H); 4.65 (m, 1H); 5.0 (m, 2H); 7.3 (m, 5H); 8.39 (m, 1H).

EXAMPLE 14

N-[4-[[[(4-Chlorophenyl)sulfonyl]amino]carbonyl]benzoyl]-L-valyl-N-[3,3-difluoro-1-(1-methylethyl)-2,4-dioxo-4-[(2-phenylethyl)amino]butyl]-L-prolinamide

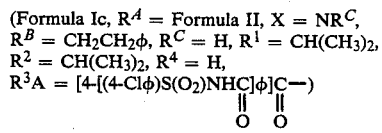
(Formula Ic, R$^A$ = Formula II, X = NR$^C$,
R$^B$ = CH₂CH₂φ, R$^C$ = H, R$^1$ = CH(CH₃)₂,
R$^2$ = CH(CH₃)₂, R$^4$ = H,
R$^{3A}$ = [4-[(4-Clφ)S(O₂)NHC]φ]C—)

DMAP (9.8 mg, 0.08 mmol) was added to a stirred solution of p-chlorobenzenesulfonamide (14 mg, 0.073 mmol) and dry CH₂Cl₂ (2.0 ml) at room temperature under N₂. WSCDI (15.34 mg, 0.08 mmol) was added to the resulting solution, followed by a portion of the product from Example 12 (47 mg, 0.073 mmol). The reaction mixture was stirred overnight at room temperature. Additional CH₂Cl₂ (20 ml) was added and the solution was washed with 1N HCl solution, and brine, and dried over MgSO₄. The solution was filtered and the filtrate was concentrated under vacuum to leave 40 mg of residue. This residue was purified by flash chromatography (low pH silica, CHCl₃:CH₃OH (99:1)) to afford the product (20.6 mg, 35%) as a white powder. TLC; R$_f$=0.32, silica gel, CHCl₃:CH₃OH:HOAc 98:2:0.1; HPLC: t$_R$=21.01 min; H₂O:CH₃OH:THF:TFA (55:35:15:0.1) 2 ml/min; (Phenomenex³ Zorbax³ C-8 analytical column, 4.6 mm×35 cm); $^1$H NMR(DMSO-d₆): 0.90 (m, 12H); 1.68–2.13 (m, 6H); 2.73 (m, 2H); 3.87 (m, 1H); 4.44 (m, 2H); 4.72 (m, 1H); 7.2 (m. 5H); 7.7 (m, 2H); 7.92 (m, 6H); 8.29 (d (J=8.57), 1H); 8.73 (d (J=7.75),1H); 9.19 (m, 1H).

EXAMPLE 15

2-[[[3,3-Difluoro-1-(1-methylethyl)-2,4-dioxooctyl-]amino]carbonyl]-1-pyrrolidinecarboxylic acid phenylmethyl ester

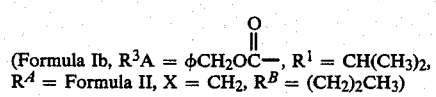

(Formula Ib, $R^3A = \phi CH_2OC-$, $R^1 = CH(CH_3)_2$, $R^4 =$ Formula II, $X = CH_2$, $R^B = (CH_2)_2CH_3$)

a. (Formula IXb, $R^3A = \phi CH_2OC-$, $R^1 = CH(CH_3)_2$)

1N NaOH (2.75 ml, 2.75 mmol) was added to a stirred solution of a product from Example 4b (1.0 g, 2.19 mmol) and methanol (15 ml) at room temperature. The resulting solution was stirred at room temperature for 4 hr. The reaction mixture was treated with water (7.5 ml) and the resulting solution was extracted with EtOAc. The aqueous layer was made acidic (pH 2) with 1N HCl. This acidic aqueous mixture was extracted with ethyl acetate. The ethyl acetate layer was washed with brine, dried (MgSO₄) filtered and the filtrate concentrated under vacuum to afford the product (0.883 g, 94.1% yield) as a white dry foam; TLC, $R_f$=0.1, silica gel, CHCl₃:CH₃OH:HOAc (95:5:0.5).

b. (Formula XIIb, $R^3A = \phi CH_2OC-$, $R^1 = CH(CH_3)_2$)

1-(3-Dimethylaminopropyl)-3-ethylcarbodiimide hydrochloride (0.24 g, 1.23 mmol) was added to a suspension of a portion of the product of Example 15a (0.48 g, 1.12 mmol), O,N-dimethylhydroxylamine hydrochloride (0.11 g, 1.12 mmol), 1-hydroxybenzotriazole (0.3 g, 2.24 mmol) and N-methylmorpholine (0.11 g, 1.12 mmol) in CH₂Cl₂(10 ml). The reaction was stirred at room temperature overnight and concentrated under vacuum. The residue was taken up in EtOAc, washed with saturated aqueous NaHCO₃, 1N aqueous HCl, and brine, then dried (Na₂SO₄), filtered and concentrated to give the product (0.42 g); TLC, $R_f$=0.38, silica gel, MeOH:CHCl₃ (5:95).

c. Formula Vb, $R^3A = \phi CH_2OC-$, $R^1 = CH(CH_3)_2$, $R^4 =$ Formula II, $X = CH_2$, $R^B = (CH_2)_2CH_3$ n-Butylmagnesium chloride (0.65 ml (2.6M in THF), 1.68 mmol) was added dropwise to a solution of a portion of the product of Example 15b (0.2 g, 0.42 mmol) in dry THF at 0° C. The reaction was stirred for 1 hr at 0° C. 1N aqueous HCl (10 ml) was added and the solution extracted with EtOAc. The combined extracts were washed with brine, dried (Na₂SO₄), filtered and concentrated to give a crude product. The product was purified by flash chromatography using EtOAc:hexane (2:3) as eluent to give the product as a white solid (0.138 g); TLC, $R_f$=0.53, silica gel, EtOAc:hexane (1:1).

d. (Formula Ib, $R^3A = \phi CH_2OC-$, $R^1 = CH(CH_3)_2$, $R^4 =$ Formula II, $X = CH_2$, $R^B = (CH_2)_2CH_3$)

Trifluoracetic acid (30 mg, 0.28 mmol) and Dess-Martin periodinane (0.24 g, 0.56 mmol) were added to a solution of a product of Example 15c (0.13 g, 0.28 mmol) in dry CH₂Cl₂ (2 ml). The reaction was stirred overnight, diluted with EtOAc, washed with saturated aqueous Na₂S₂O₃, saturated aqueous NaHCO₃, and brine, dried (Na₂SO₄), filtered and concentrated to give a crude product. The product was purified by flash chromatography using as eluent EtOAc:hexane (30:70) to give the product as a clear oil (0.125 g, 100%); TLC, $R_f$=0.3, silica gel, EtOAc:hexane (30:70).

Analysis calculated for: $C_{24}H_{32}F_2N_2O_5 \cdot 0.5H_2O$: C, 60.62; H, 6.99; N, 5.89. Found: C, 60.51; H, 6.80; N, 5.82.

EXAMPLE 16

3-[[[3,3-Difluoro-1-(1-methylethyl)-5-phenyl-2,4-dioxopentyl]amino]carbonyl]-1-pyrrolidinecarboxylic acid phenylmethyl ester

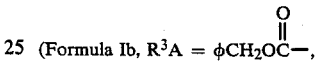

(Formula Ib, $R^3A = \phi CH_2OC-$, $R^1 = CH(CH_3)_2$, $R^4 =$ Formula II, $X = CH_2$, $R^B = \phi$)

a. Formula Vb, $R^3A = \phi CH_2OC-$, $R^1 = CH(CH_3)_2$, $R^4 =$ Formula II, $X = CH_2$, $R^B = \phi$ Using the method of Example 15c, product prepared using the method of Example 15b was allowed to react with benzylmagnesium chloride to give the crude product which was used without further purification; TLC, $R_f$=0.58, silica gel, MeOH:CHCl₃ (5:95).

b. Formula Ib, $R^3A = \phi CH_2OC-$, $R^1 = CH(CH_3)_2$, $R^4 =$ Formula II, $X = CH_2$, $R^B = \phi$ Using the method of Example 15d, the product of Example 16a was oxidized to afford, after purification by MPLC (Si60 Lichroprep Size B, EtOAc:hexane (35:65)) and repurification using EtOAc:hexane (30:70), the title product (50%); TLC, $R_f$=0.41, silica gel, EtOAc:hexane (40:60); High Resolution Mass Spectrum (EI), theoretical mass: 500.2122; measured mass: 500.2135.

EXAMPLE 17

2-[[[3,3-Difluoro-1-(1-methylethyl)-6-phenyl-2,4-dioxohexyl]amino]carbonyl]-1-pyrrolidinecarboxylic acid phenylmethyl ester

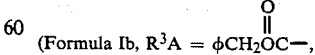

(Formula Ib, $R^3A = \phi CH_2OC-$, $R^1 = CH(CH_3)_2$, $R^4 =$ Formula II, $X = CH_2$, $R^B = CH_2\phi$)

a. Formula Vb, $R^3A = \phi CH_2OC-$, $R^1 = CH(CH_3)_2$, $R^4 =$ Formula II, $X = CH_2$, $R^B = CH_2\phi$ (2-Chloroethyl)benzene (0.79 ml) was added dropwise to a stirred mixture of Mg (0.16 g) in dry THF (5 ml) under $N_2$. The mixture was heated at reflux for 2 hr; the dark solution was cooled to room temperature and added via syringe to a pre-cooled (0°) solution of a portion of the product of Example 15b (0.7 g) in THF (5 ml). The reaction was stirred for 1 hr at 0° before 1N HCl (7 ml) was added and the solution extracted with EtOAc. The combined extracts were washed (brine), dried ($Na_2SO_4$), and concentrated to give the crude product. The product was purified by MPLC (Si60 Lichroprep Size B, EtOAc:hexane (30:70)) to give the product as a white solid (0.48 g); TLC, $R_f$=0.49, silica gel, EtOAc:hexane (50:50).

b. Formula Ib, $R^3A = \phi CH_2O\overset{O}{\underset{\|}{C}}-$, $R^1CH(CH_3)_2$, $R^4 = $ Formula II, $X = CH_2$, $R^B = CH_2\phi$ Using the method of Example 15d, the product of Example 17a was oxidized to afford the title product (100%); TLC, $R_f$=0.44, silica gel, EtOAc:hexane (50:50).

Analysis calculated for $C_{28}H_{32}F_2N_2O_5 \cdot 1.5\ H_2O$: C, 62.10; H, 5.51; N, 5.17. Found: C, 62.14; H, 5.97; N, 6.06.

EXAMPLE 18

2-[[[3,3-Difluoro-1-(1-methylethyl)-7-phenyl-2,4-dioxoheptyl]amino]carbonyl]-1-pyrrolidinecarboxylic acid phenylmethyl ester

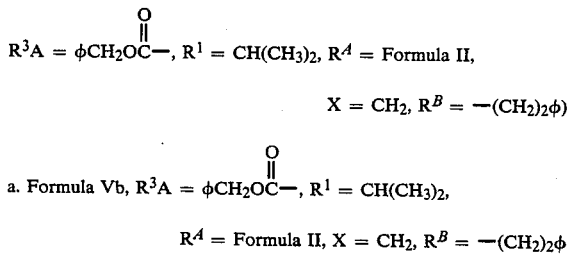

a. Formula Vb, $R^3A = \phi CH_2O\overset{O}{\underset{\|}{C}}-$, $R^1 = CH(CH_3)_2$, $R^4 = $ Formula II, $X = CH_2$, $R^B = -(CH_2)_2\phi$ Using the method of Example 17a, product prepared using the method of Example 15b was allowed to react with 3-phenyl-1-propylmagnesium bromide to afford, after purification by MPLC (Si60 Lichroprep Size B, EtOAc:hexane (30:70), the product (42%); TLC, $R_f$=0.33, silica gel, EtOAc:hexane (40:60).

b. Formula Ib, $R^3A = \phi CH_2O\overset{O}{\underset{\|}{C}}-$, $R^1 = CH(CH_3)_2$, $R^4 = $ Formula II, $X = CH_2$, $R^B = -(CH_2)_2\phi$ Using the method of Example 15d, the product of Example 18a was oxidized to afford, after purification by MPLC (Si60 Lichroprep Size B, EtoAc/hexane (30:70)), the title product (86%); TLC, $R_f$=0.53, silica gel, EtOAc:hexane (40:60).

Analysis calculated for: $C_{29}H_{34}F_2N_2O_5 \cdot 0.75\ H_2O$: C, 64.25; H, 6.60; N, 5.17. Found: C, 64.28; H, 6.35; N, 4.94.

EXAMPLE 19

2-[[[3,3-Difluoro-5-methyl-1-(1-methylethyl)-2,4-dioxoheptyl]amino]carbonyl]-1-pyrrolidinecarboxylic acid phenylmethyl ester

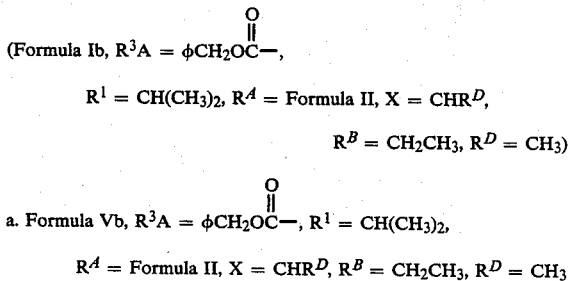

a. Formula Vb, $R^3A = \phi CH_2O\overset{O}{\underset{\|}{C}}-$, $R^1 = CH(CH_3)_2$, $R^4 = $ Formula II, $X = CHR^D$, $R^B = CH_2CH_3$, $R^D = CH_3$ Using the method of Example 15c, product prepared using the method of Example 15b was allowed to react with sec-butylmagnesium chloride to give the crude product which was used without further purification; TLC, $R_f$=0.42, silica gel, EtOAc:hexane (40:60).

b. Formula Ib, $R^3A = \phi CH_2O\overset{O}{\underset{\|}{C}}-$, $R^1 = CH(CH_3)_2$, $R^4 = $ Formula II, $X = CHR^D$, $R^B = CH_2CH_3$, $R^D = CH_3$ Using the method of Example 15d, the product of Example 19a was oxidized to afford, after purification by MPLC (Si60 Lichroprep Size B, EtOAc:hexane (30:70)), the title product (43%); TLC, $R_f$=0.53, silica gel, EtOAc:hexane (40:60).

Analysis calculated for: $C_{24}H_{32}F_2N_2O_5 \cdot 0.75\ H_2O$: C, 60.05; H, 7.03; N, 5.84. Found: C, 60.11; H, 6.67; N, 5.57.

EXAMPLE 20

N-[(Phenylmethoxy)carbonyl]-L-valyl-N-[3,3-difluoro-1-(1-methylethyl)-7-phenyl-2,4-dioxoheptyl]-L-prolinamide (Formula Ic, $R^3A = \phi CH_2O\overset{O}{\underset{\|}{C}}-$, $R^4 = H$, $R^2 = CH(CH_3)_2$, $R^1 = CH(CH_3)_2$, $R^4 = $ Formula II, $X = CH_2$, $R^B = -(CH_2)_2\phi$)

a. N-[3,3-Difluoro-1-(1-methylethyl)-7-phenyl-2,4-dioxoheptyl]-L-prolinamide

A mixture of a portion of the product of Example 18a (2.6 g, 4.9 mmol) and 10% Pd/C (0.26 g) in absolute ethanol was stirred under hydrogen (1 bar) for 3 hr. An additional portion of 10% Pd/C (0.13 g) was added and stirring was continued under hydrogen (1 bar) for 1 hr. The reaction mixture was then filtered through a pad of diatomaceous earth and the filtrate was concentrated under vacuum to give the product (1.84 g) as a clear oil; TLC, $R_f$=0.28, silica gel, MeOH:CHCl$_3$ (5:95).

b. Formula Vc, $R^3A = \phi CH_2O\overset{O}{\underset{\|}{C}}-$, $R^4 = H$,
$R^2 = CH(CH_3)_2$, $R^1 = CH(CH_3)_2$,
$R^4 = $ Formula II, $X = CH_2$, $R^B = -(CH_2)_2\phi$ WSCDI (0.9 g) was added to a stirred solution of the product of Example 20a (1.7 g), benzyloxycarbonyl-L-valine (1.08 g) and HOBT (1.16 g) in CH$_2$Cl$_2$ (20 ml). The reaction mixture was stirred for 4 days at room temperature. The CH$_2$Cl$_2$ was removed under vacuum. The residue was partitioned between EtOAc and saturated aqueous NaHCO$_3$; the EtOAc layer was washed (1M aqueous HCl and brine); dried (Na$_2$SO$_4$), and concentrated under vacuum to afford, after column chromatography (EtOAc:hexane (40:60), then (50:50)), the product (2.08 g); TLC, R$_f$=0.49, silica gel, EtOAc:hexane (50:50).

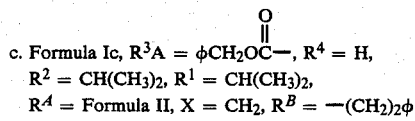

c. Formula Ic, R$^3$A = φCH$_2$OC(O)—, R$^4$ = H,
R$^2$ = CH(CH$_3$)$_2$, R$^1$ = CH(CH$_3$)$_2$,
R$^A$ = Formula II, X = CH$_2$, R$^B$ = —(CH$_2$)$_2$φ

Using the method of Example 15d, a portion of the product of Example 20b was oxidized to afford, after purification by column chromatography (EtOAc:hexane (25:65)), the product (100%); TLC, R$_f$=0.63, silica gel, EtOAc:hexane (50:50).

Analysis calculated for: C$_{34}$H$_{43}$F$_2$N$_3$O$_6$·0.5 H$_2$O: C, 64.14; H, 6.96; N, 6.60. Found: C, 64.01; H, 6.88; N, 6.37.

EXAMPLE 21

N-[4-(Phenylsulfonylaminocarbonyl)benzoyl]-L-valyl-N-[3,3-difluoro-1-(1-methylethyl)-7-phenyl-2,4-dioxoheptyl]-L-prolinamide

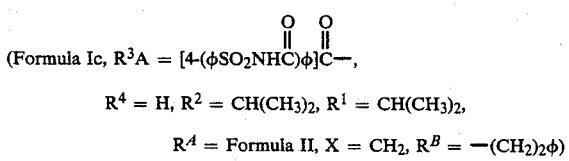

(Formula Ic, R$^3$A = [4-(φSO$_2$NHC(O))φ]C(O)—,
R$^4$ = H, R$^2$ = CH(CH$_3$)$_2$, R$^1$ = CH(CH$_3$)$_2$,
R$^A$ = Formula II, X = CH$_2$, R$^B$ = —(CH$_2$)$_2$φ)

a. Di-t-butyl terephthalate

Pyridine (20 g) was added to a stirred mixture of terephthaloyl chloride (25 g) and t-butanol (74 g). The reaction temperature rose to 60° and stirring was continued for 2 hr as the reaction cooled to room temperature. After stirring overnight the solid cake was treated with water and filtered. The solid was dissolved in ether, the ether solution was washed with saturated aqueous NaHCO$_3$ and concentrated under vacuum to give the crude product which was crystallized from ethanol/water to give the product as white needles (18.49 g); mp 117°–118°.

b. Terephthalic acid mono-t-butyl ester

A solution of KOH (4.05 g) in t-butanol (60 ml) was added to a stirred solution of the product of Example 21a (18 g) in t-butanol (86 ml) at 50°. Stirring was continued for 3.5 hr at 50°. Ether was added and the reaction mixture was filtered. The solid was dissolved in H$_2$O, the aqueous solution was extracted with CHCl$_3$ and the aqueous layer was acidified with 3M aqueous HCl. The white precipitate which formed was filtered and dried at 60° to give the product as a white solid (10.19 g); NMR (DMSO-d$_6$): 8.01(s, 4H), 1.56(s, 9H).

c. 4-(Phenylsulfonylaminocarbonyl)benzoic acid t-butyl ester

WSCDI (9.49 g) and then the product of Example 21b (10.0 g) were added to a stirred solution of DMAP (6.05 g) and benzenesulfonamide (7.07 g) in CH$_2$Cl$_2$ (500 ml). The reaction was stirred at room temperature overnight, filtered, the filtrate concentrated under vacuum and the residue dissolved in EtOAc. The organic solution was washed (1M aqueous HCl, saturated aqueous NaHCO$_3$ and brine), dried (MgSO$_4$) and concentrated. The sticky residue was dissolved in ethanol, and H$_2$O was added until the product precipitated. The precipitate was filtered and dried to give the product as a white powder (9.75 g); mp 141°–143°.

d. 4-(Phenylsulfonylaminocarbonyl)benzoic acid

The product of Example 21c (9.0 g) was added to TFA (115 ml) at 0° under an atmosphere of N$_2$. The reaction was stirred at 0° for 3 hr and poured into ice/water (400 ml). The precipitate was filtered and recrystallized from ethanol/water to give the product as white crystals (6.0 g); mp 259°–261°.

e. L-Valyl-N-[3,3-difluoro-1-(1-methylethyl)-7-phenyl-2,4-dioxoheptyl]-L-prolinamide A mixture of a portion of the product of Example 20b (1.77 g) and 10% Pd/C (0.36 g) in absolute ethanol (50 ml) was stirred at room temperature under H$_2$ (1 bar) for 3 hr. The mixture was filtered through a pad of diatomaceous earth and the filtrate was concentrated to give the product (1.42 g) as a white foam, which was used without further purification.

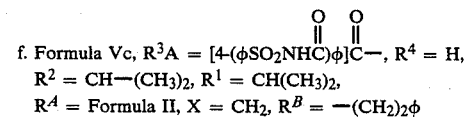

f. Formula Vc, R$^3$A = [4-(φSO$_2$NHC(O))φ]C(O)—, R$^4$ = H,
R$^2$ = CH—(CH$_3$)$_2$, R$^1$ = CH(CH$_3$)$_2$,
R$^A$ = Formula II, X = CH$_2$, R$^B$ = —(CH$_2$)$_2$φ

WSCDI (0.61 g) was added to a stirred solution of the product of Example 21e (1.42 g), a portion of the product of Example 21d (0.8 g), and HOBT (0.77 g) in THF (201 ml); and the mixture was stirred at room temperature for 24 hr. The THF was removed under vacuum. The residue was taken up in EtOAc, washed (1M aqueous HCl and brine), dried (Na$_2$SO$_4$), and concentrated to give the crude product. The product was purified by flash chromatography (low pH silica gel) using as eluant a gradient of MeOH:CHCl$_3$ [(0:100), (1:99), (2.5:97.5), (5:95)] to give the product as a pale yellow oil (1.72 g); TLC, R$_f$=0.44, silica gel, MeOH:CHCl$_3$:HOAc (2:98:0.1).

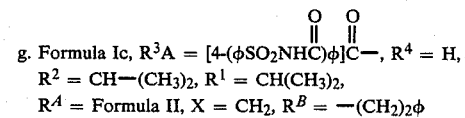

g. Formula Ic, R$^3$A = [4-(φSO$_2$NHC(O))φ]C(O)—, R$^4$ = H,
R$^2$ = CH—(CH$_3$)$_2$, R$^1$ = CH(CH$_3$)$_2$,
R$^A$ = Formula II, X = CH$_2$, R$^B$ = —(CH$_2$)$_2$φ

Using the method of Example 15d, the product of Example 21f was oxidized to afford, after purification by flash chromatography (low pH silica gel, gradient elution using MeOH:CHCl$_3$ [(0:100), (1:99), (2.5:97.5), (5:95)]) and further purification by dissolving the product in a mixture of MeOH (50 ml) and 1M aqueous HCl (25 ml), removal of MeOH under vacuum, extraction of the remaining aqueous layer with ether and concentration of the ether layer to give the product, a pale yellow solid (1.34 g); HPLC, t$_R$=11.70 min; H$_2$O:CH$_3$CN:THF:TFA:triethylamine (55:35:15:0.1:0.2), FR=0.5 ml/min; (Phenomenex ® Zorbax ® C-8 anayltical column, 4.6 mm×25 cm).

Analysis calculated for: C$_{40}$H$_{46}$F$_2$N$_4$O$_8$S·0.75 H$_2$O: C, 60.48; H, 6.03; N, 7.05. Found: C, 60.54; H, 6.00; N, 6.93.

EXAMPLE 22

N-(4-Carboxybenzoyl)-L-valyl-N-[3,3-difluoro-1-(1-methylethyl)-2-oxo-6-phenylhexyl]-L-prolinamide

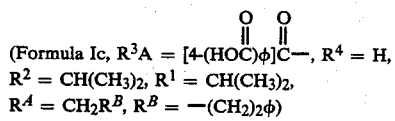
(Formula Ic, $R^3A = [4\text{-}(HOC)\phi]\overset{O}{\underset{\|}{C}}\text{---}$, $R^4 = H$,
$R^2 = CH(CH_3)_2$, $R^1 = CH(CH_3)_2$,
$R^A = CH_2R^B$, $R^B = \text{---}(CH_2)_2\phi$)

a. Formula XXV, $R^X = CH_2CH_3$, $R^A = CH_2R^B$, $R^B = \text{---}(CH_2)_2\phi$ 1-Bromo-3-phenylpropane (26 g) was added dropwise to a stirred mixture of Mg (3.4 g) in THF (130 ml) under an atmosphere of $N_2$ and heated at reflux for 2 hr. The reaction mixture was transferred slowly via cannula (over about 1 hr) to a pre-cooled ($-10°$) solution of diethyl oxalate (36.9 g) in THF (70 ml) under an atmosphere of $N_2$. Enough 1M aqueous HCl (about 90 ml) was added to the reaction mixture to obtain a solution of pH 3–4. After the organic and aqueous layers were separated, the aqueous layer was extracted with $CH_2Cl_2$. The combined organic layers were washed (brine), dried ($Na_2SO_4$), and concentrated to give a pale yellow oil which was purified by bulb to bulb distillation, (27–40 Pa, oven temperature 120°–150°) to give a pale yellow liquid (18.7 g).

b. Formula XXIV, $R^X = CH_2CH_3$, $R^A = CH_2R^B$, $R^B = \text{---}(CH_2)_2\phi$ Using the procedure of Example 13b, a portion of the product of Example 22a was allowed to react with dimethylaminosulfurtrifluoride to afford, after purification by bulb distillation (67 Pa, oven temperature 75°–80°), the product (87%) as a very pale yellow liquid; TLC, $R_f=0.5$, silica gel $CH_2Cl_2$/hexane (50:50).

c. Formula XX, $R^A = CH_2R^B$, $R^B = \text{---}(CH_2)_2\phi$

Using the procedure of Example 13c, a portion of the product of Example 22b was allowed to react with diisobutylaluminum hydride to give the product as a clear oil (96%) which was used without further purification; TLC, $R_f=0.13$, silica gel, $CH_2Cl_2$.

d. Formula XXI, $R^1 = CH(CH_3)_2$, $R^A = CH_2R^B$, $R^B = \text{---}(CH_2)_2\phi$ (WARNING: potentially explosive)

2-Methyl-1-nitropropane (WARNING: potentially explosive) (Formula XIX, $R^1 = CH(CH_3)_2$) (1.9 g), $K_2CO_3$ (2.5 g), and a portion of the product of Example 22c (4.5 g) were stirred at room temperature for 72 hr. Water (20 ml) was added, and sufficient 1M aqueous HCl was added to neutralize the solution. The solution was extracted with ether; the combined ether extracts were washed (brine), dried ($Na_2SO_4$), and concentrated. The crude product was purified by flash chromatography using as eluant a gradient of hexane:$CH_2Cl_2$ [(100:0), (80:20), (70:30)] to give the product as a yellow solid (2.9 g); TLC, $R_f=0.51, 0.56$, silica gel, $CH_2Cl_2$:hexane (75:25).

e. Formula XXII, $R^1 = CH(CH_3)_2$, $R^A = CH_2R^B$, $R^B = \text{---}(CH_2)_2\phi$ A mixture of a portion of the product of Example 22d (2.7 g) and 10% Pd/C (0.27 g) in absolute ethanol (50 ml) was shaken in a hydrogenation apparatus under $H_2$ (3 bar) at room temperature for 36 hr. After 24 hr, the reaction was interrupted and 10% Pd/C (0.27 g) was added. The reaction mixture was filtered through a pad of diatomaceous earth. The filtrate was concentrated under vacuum, the residue was taken up in absolute ethanol (50 ml) and 10% Pd/C was added (0.5 g). The reaction mixture was shaken under $H_2$ (3 bar) for 90 hr.

After 18 hr the reaction was interrupted and additional 10% Pd/C (0.5 g) was added. The reaction was filtered through a pad of diatomaceous earth and the filtrate was concentrated under vacuum. The residue was taken up in ether and extracted with 1M aqueous HCl. The combined aqueous extracts were washed with ether and neutralized by addition of solid $Na_2CO_3$. The neutralized solution was extracted with ether; the combined organic extracts were washed (brine), dried ($Na_2SO_4$), and concentrated to give the product as a white solid (1.32 g); TLC, $R_f=0.30, 0.43$, silica gel, MeOH:CHCl$_3$ (5:95).

f. L-Valyl-L-proline t-butyl ester

Using the method of Example 1d, but using absolute ethanol as solvent, product prepared by the method of Example 3a was hydrogenated for 4 hr to afford the product (72%); TLC, $R_f=0.12$, silica gel, MeOH:CHCl$_3$ (5:95).

g. N-[4-(Methoxycarbonyl)benzoyl]-L-valyl-L-proline t-butyl ester

Using the method of Example 6c, product prepared by the method of Example 22f was allowed to react with product prepared by the method of Example 11a to afford, after purification by flash chromatography (CHCl$_3$, MeOH:CHCl$_3$ (2:98)), the product (49%), TLC, $R_f=0.6$, silica gel, MeOH:CHCl$_3$ (3:97).

h. N—[4-(Methoxycarbonyl)benzoyl]-L-valyl-L-proline

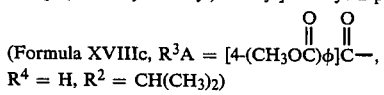
(Formula XVIIIc, $R^3A = [4\text{-}(CH_3OC)\phi]\overset{O}{\underset{\|}{C}}\text{---}$,
$R^4 = H$, $R^2 = CH(CH_3)_2$)

Using the method of Example 10b, the product of Example 22g was hydrolyzed to afford the product (71%); TLC, $R_f=0.3$, silica gel, $CH_3OH$:CHCl$_3$:HOAc (10:90:0.1).

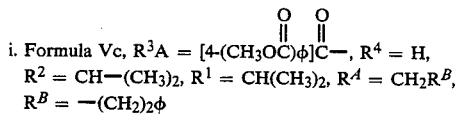
i. Formula Vc, $R^3A = [4\text{-}(CH_3OC)\phi]\overset{O}{\underset{\|}{C}}\text{---}$, $R^4 = H$,
$R^2 = CH\text{---}(CH_3)_2$, $R^1 = CH(CH_3)_2$, $R^A = CH_2R^B$,
$R^B = \text{---}(CH_2)_2\phi$ Isobutyl chloroformate (0.22 ml) was added under $N_2$ to a pre-cooled ($-45°$) solution of the product of Example 22h (0.64 g) and N-methylmorpholine (0.2 ml) in dry THF (20 ml); and the mixture was allowed to stir for 1 hr at $-45°$. A solution of the product of Example 22e (0.46 g) in dry THF (10 ml) was added dropwise, and the resulting solution was allowed to warm slowly to room temperature overnight. The mixture was filtered and the THF was removed under vacuum. The residue was taken up on EtOAc; and the organic solution washed (1M aqueous HCl, saturated aqueous NaHCO$_3$ and brine), dried ($Na_2SO_4$), and concentrated to give the product (0.93 g); TLC, $R_f=0.60$, silica gel, MeOH:CHCl$_3$ (5:95).

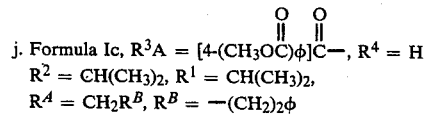
j. Formula Ic, $R^3A = [4\text{-}(CH_3OC)\phi]\overset{O}{\underset{\|}{C}}\text{---}$, $R^4 = H$
$R^2 = CH(CH_3)_2$, $R^1 = CH(CH_3)_2$,
$R^A = CH_2R^B$, $R^B = \text{---}(CH_2)_2\phi$ Using the procedure of Example 15d, except using 3 mole equivalents of Dess-Martin periodinane, the product of Example 22i was oxidized to afford the product (100%); TLC, $R_f=0.6$, silica gel, MeOH:CHCl$_3$ (2:98).

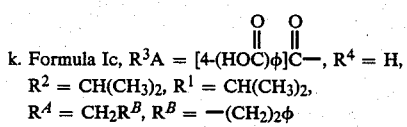

k. Formula Ic, $R^3A = [4-(HO)\phi]\overset{O}{\underset{\|}{C}}-$, $R^4 = H$,
$R^2 = CH(CH_3)_2$, $R^1 = CH(CH_3)_2$,
$R^A = CH_2R^B$, $R^B = -(CH_2)_2\phi$ One molar aqueous NaOH (1.65 ml) was added to a solution of the product of Example 22j (0.92 g) in a mixture of MeOH (10 ml) and H$_2$O (8.5 ml). The mixture was stirred overnight at room temperature and additional 1M aqueous NaOH was added to bring the solution to pH 12. The mixture was stirred overnight, additional 1M aqueous NaOH was added to return the solution to pH 12, and stirring was continued at room temperature overnight. 1M aqueous HCl (2 ml) was added, and the reaction was diluted with H$_2$O and extracted with EtOAc. The combined organic extracts were washed (brine), dried (Na$_2$SO$_4$), and concentrated. The crude product was purified by flash chromatography on acidic silica gel using as eluent a gradient of ether:EtOAc [(100:0), (50:50) and (0:100)] to give the product (0.68 g); TLC, $R_f=0.47$, silica gel, Et$_2$O:HOAc (99.9:0.1).

Analysis calculated for C$_{33}$H$_{41}$F$_2$N$_3$O$_6$·0.5H$_2$O: C, 63.65; H, 6.79; N, 6.75. Found: C, 63.76; H, 6.70; N, 6.50.

EXAMPLE 23

N-[4-[[(Methylsulfonyl)amino]carbonyl]benzoyl]-L-valyl-N-[3,3-difluoro-1-(1-methylethyl)-2-oxo-6-phenylhexyl]-L-prolinamide

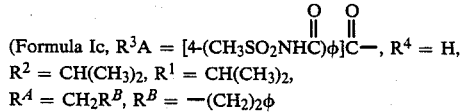

(Formula Ic, $R^3A = [4-(CH_3SO_2NHC)\phi]\overset{O}{\underset{\|}{C}}-$, $R^4 = H$,
$R^2 = CH(CH_3)_2$, $R^1 = CH(CH_3)_2$,
$R^A = CH_2R^B$, $R^B = -(CH_2)_2\phi$ WSCDI (0.25 g) was added to a stirred mixture of DMAP (0.15 g), methanesulfonamide (0.12 g), and a portion of the product of Example 22k (0.6 g) in CH$_2$Cl (20 ml). The mixture was stirred at room temperature for 24 hr, the CH$_2$Cl$_2$ was removed under vacuum, and EtOAc was added. The EtOAc solution was washed (1M aqueous HCl and brine), dried (Na$_2$SO$_4$), and concentrated. The crude product was purified by flash chromatography on acidic silica gel using as eluent a gradient of ether:EtOAc [(100:0), (50:50), (0:100)] to give the product (0.51 g); HPLC; $t_R=17.07$, H$_2$O:CH$_3$CN:THF:TFA (55:35:15:0.1), FR=1.5 ml/min (Zorbax ODS analytical column, 7.6 mm+25 cm).

Analysis calculated for C$_{34}$H$_{44}$F$_2$N$_4$O$_7$S·0.5H$_2$O: C, 58.36; H, 6.48; N, 8.01. Found: C, 58.53; H, 6.18; N, 7.79.

EXAMPLE 24

N-[4-[[[(4-Chlorophenyl)sulfonyl]amino]carbonyl]benzoyl]-L-valyl-N-[3,3-difluoro-1-(1-methylethyl)-2-oxo-6-phenylhexyl]-L-prolinamide

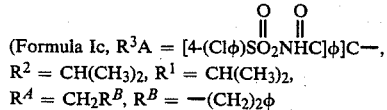

(Formula Ic, $R^3A = [4-(Cl\phi)SO_2NHC]\phi]C-$,
$R^2 = CH(CH_3)_2$, $R^1 = CH(CH_3)_2$,
$R^A = CH_2R^B$, $R^B = -(CH_2)_2\phi$ -continued

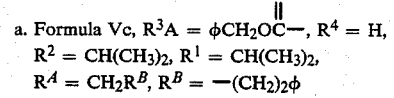

a. Formula Vc, $R^3A = \phi CH_2O\overset{O}{\underset{\|}{C}}-$, $R^4 = H$,
$R^2 = CH(CH_3)_2$, $R^1 = CH(CH_3)_2$,
$R^A = CH_2R^B$, $R^B = -(CH_2)_2\phi$ Using the procedure of Example 22i, product of Example 22e was coupled with product of Example 3b to afford, after purification by MPLC (Lichroprep Si60, Size B, eluted with EtOAc:hexane (50:50)), the product (58%); TLC, $R_f=0.38$, silica gel, EtOAc:hexane (50:50).

b. L-Valyl-N-[3,3-difluoro-2-hydroxy-1-(1-methylethyl)-6-phenylhexyl]-L-prolinamide A mixture of the product of Example 24a (0.9 g) and 10% Pd/C (0.1 g) in absolute ethanol (20 ml) was stirred at room temperature under H$_2$ (1 bar) overnight. The mixture was filtered through a pad of diatomaceous earth and the filtrate was concentrated to give the product (0.65 g); TLC, $R_f=0.05$, silica gel, EtOAc:hexane (50:50).

c. 1,1-Dimethylethyl 4-[(4-chlorophenyl)sulfonylaminocarbonyl]benzoate

A 5-liter 3-neck round bottom flask was equipped with a mechanical stirrer and nitrogen inlet. Methylene chloride (2 liters) was placed in the reaction flask and terephthalic acid mono-t-butyl ester (127.5 g), 4-dimethylaminopyridine (70.06 g), and 4-chlorobenzenesulfonamide (110.04 g) were added sequentially using methylene chloride (400 ml) to wash down the solids. 1-(3-Dimethylaminopropyl)-3-ethylcarbodiimide hydrochloride was added in portions over 10 min using methylene chloride (100 ml) to wash down the solid. After the reaction mixture was stirred overnight at room temperature, it was evaporated to dryness. The residue was partitioned between ethyl acetate and water. The organic solution was washed with 20% (w/v) aqueous citric acid, saturated aqueous NaHCO$_3$ and brine; dried (Na$_2$SO$_4$); and evaporated to a white solid. After drying in a vacuum oven at 50°, the ester (277 g, 100%) was obtained in a sufficiently pure state to be used directly for the next step; TLC, $R_f=0.43$, methanol:chloroform (15:85). (Further purification was possible by recrystallization from ethanol/water; mp above 300°).

d. 4-[(4-Chlorophenyl)sulfonylaminocarbonyl]benzoic acid

A 3-liter 3-neck round bottom flask was equipped with a mechanical stirrer and a CaCl$_2$ drying tube. Trifluoroacetic acid (1300 g) was added and cooled to 0°, and the product of Example 1n (79.5 g) was added. Initially, the solid dissolved, giving a clear solution. After 10-15 min, a heavy precipitate of product formed; and it was difficult to stir the reaction mixture Vigorous stirring with the mechanical stirrer was essential to drive the reaction to completion. The reaction mixture was stirred at 0°-5° for 1 hr before it was poured into 1500 ml of ice/water and stirred for 2 hr. The resulting solid was filtered and dried. The white solid (61.5 g, 91%) obtained was recrystallized from 1600 ml absolute ethanol/1600 ml water to yield the benzoic acid (54 g, 80%) as white needles; mp 286°-288°; TLC, $R_f=0.7$, MeOH:CHCl$_3$:acetic acid (10:90:1).

e. Formula Vc, $R^3A = [4-[(4-Cl\phi)SO_2NHC]\phi]\overset{\overset{O}{\|}}{C}\overset{O}{\underset{\|}{-}}$,
$R^4 = H$, $R^2 = CH(CH_3)_2$, $R^1 = CH(CH_3)_2$,
$R^A = CH_2R^B$, $R^B = -(CH_2)_2\phi$ WSCDI (0.29 g) was added to a stirred mixture of HOBT (0.38 g), product of Example 24b (0.65 g) and product of Example 24d (0.47 g) in CH₂Cl₂ (10 ml). The mixture was stirred at room temperature for 3 days. The CH₂Cl₂ was removed under vacuum; the residue was taken up in EtOAc, washed (saturated NaHCO₃, 1M aqueous HCl and brine), dried (Na₂SO₄), and concentrated. The crude product was purified by flash chromatography on acidic silica gel using as eluant a gradient of ether:EtOAc [(100:0), (50:50), (0:100)] to give the product (1.09 g); TLC, R_f=0.42, silica gel, ether:EtOAc:HOAc (50:50:0.5).

f. Formula Ic, $R^3A = [4\text{-}(CH_3SO_2NHC)\phi]\overset{\overset{O}{\|}}{C}\overset{O}{\underset{\|}{-}}$,
$R^4 = H$, $R^2 = CH(CH_3)_2$, $R^1 = CH(CH_3)_2$,
$R^A = CH_2R^B$, $R^B = -(CH_2)_2\phi$ A mixture of the product of Example 24e (1.09 g), Dess-Martin periodinane (1.78 g), and TFA (0.11 ml) in CH₂Cl₂ (15 ml) was stirred overnight. The mixture was diluted with EtOAc and washed [saturated aqueous NaHCO₃:saturated aqueous Na₂S₂O₃ (1:1), saturated aqueous NaHCO₃, and brine], dried (Na₂SO₄), and concentrated. The crude product was purified by flash chromatography on acidic silica gel using as eluant a gradient of CHCl₃:MeOH [(100:0), (98:2), (96:4), (90:10)] to give the product (0.74 g); HPLC: t_R=10.66, 11.80, CH₃CN:0.01M K₂HPO₄/H₃PO₄ pH 3 (50:50), FR=2 ml/min (Zorbax ODS analytical column, 4.6 mm×25 cm).

Analysis calculated for C₃₉H₄₅ClF₂N₄O₇S.0.5H₂O: C, 58.82; H, 5.82; N, 7.04. Found: C, 58.54; H, 5.87; N, 6.88.

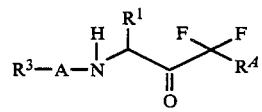 Ia

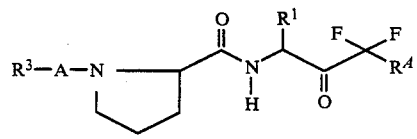 Ib

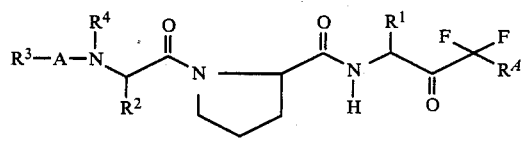 Ic

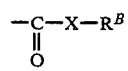 II

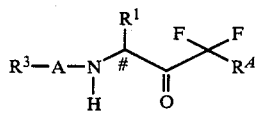 IIIa

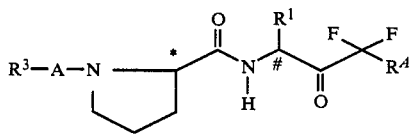 IIIb

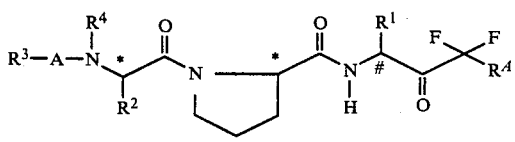 IIIc

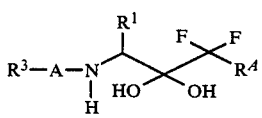 IVa

-continued
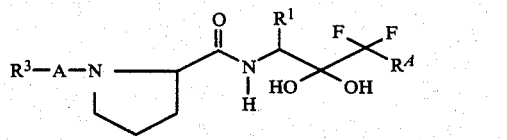  IVb
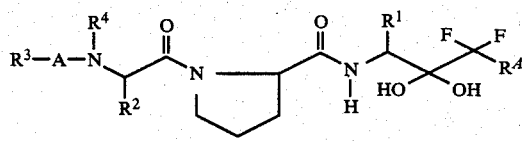  IVc
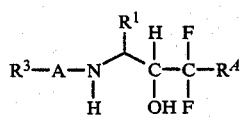  Va
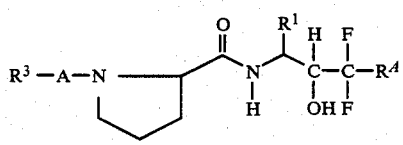  Vb
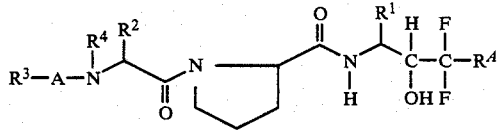  Vc
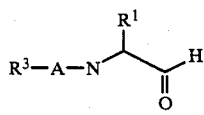  VIa
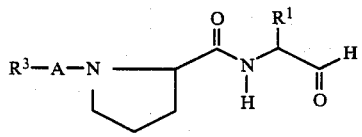  VIb
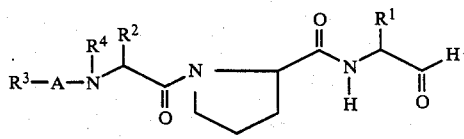  VIc
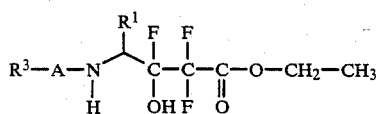  VIIa
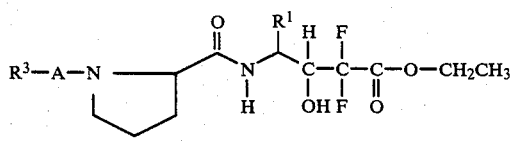  VIIb
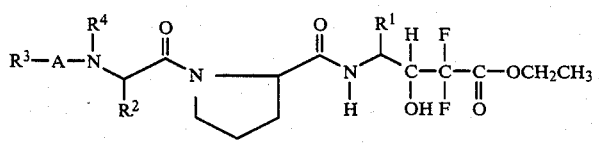  VIIc
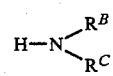  Vd -continued
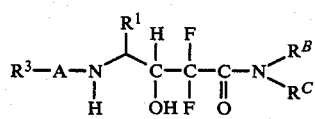 VIIIa
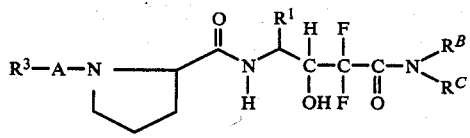 VIIIb
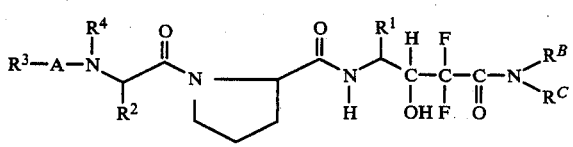 VIIIc
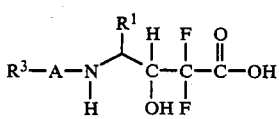 IXa
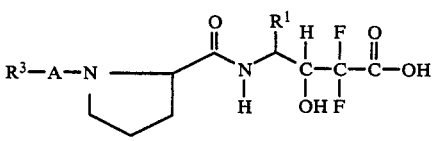 IXb
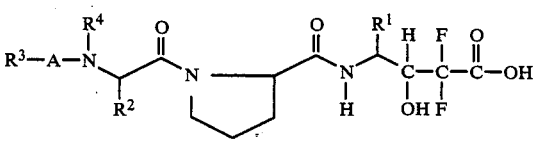 IXc
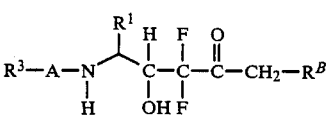 Xa
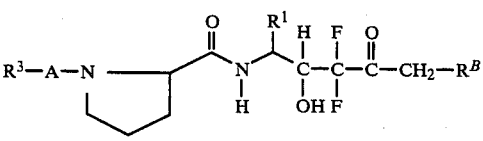 Xb
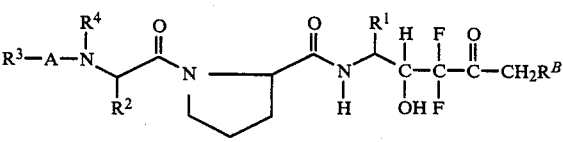 Xc
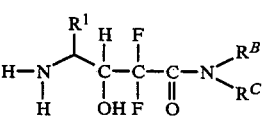 XIa
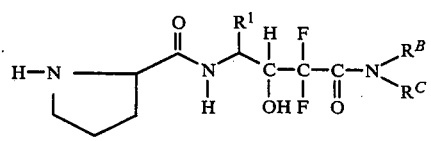 XIb -continued
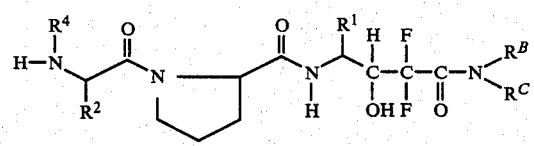 XIc
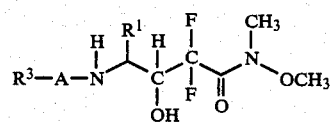 XIIa
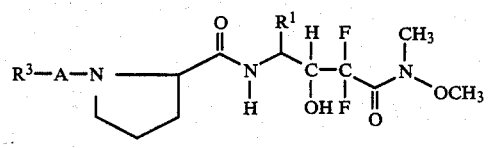 XIIb
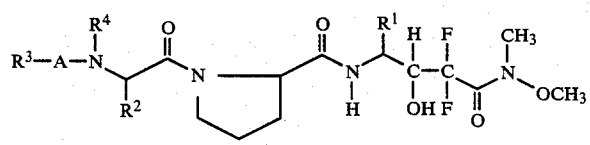 XIIc
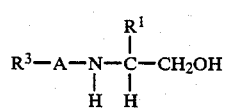 XIVa
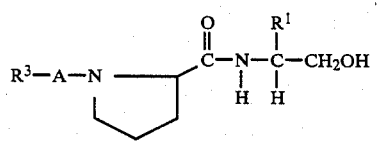 XIVb
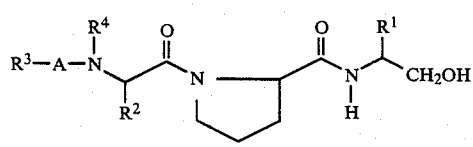 XIVc
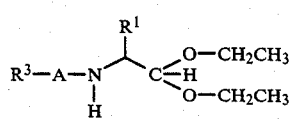 XVa
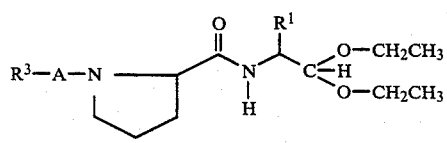 XVb
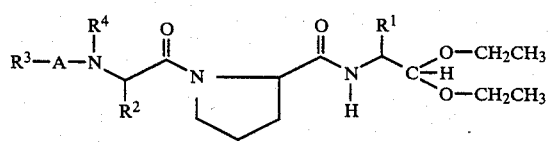 XVc
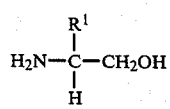 XVI

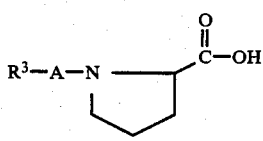
XVIIb
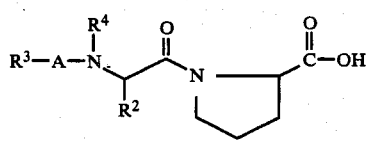
XVIIc
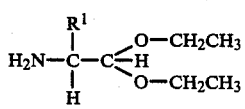
XVIIIa
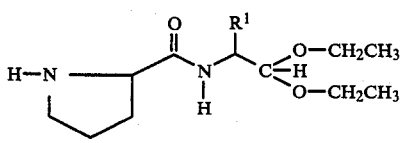
XVIIIb
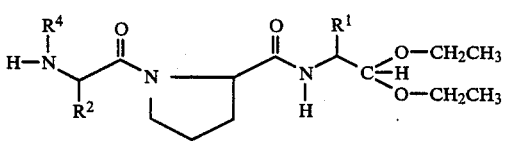
XVIIIc
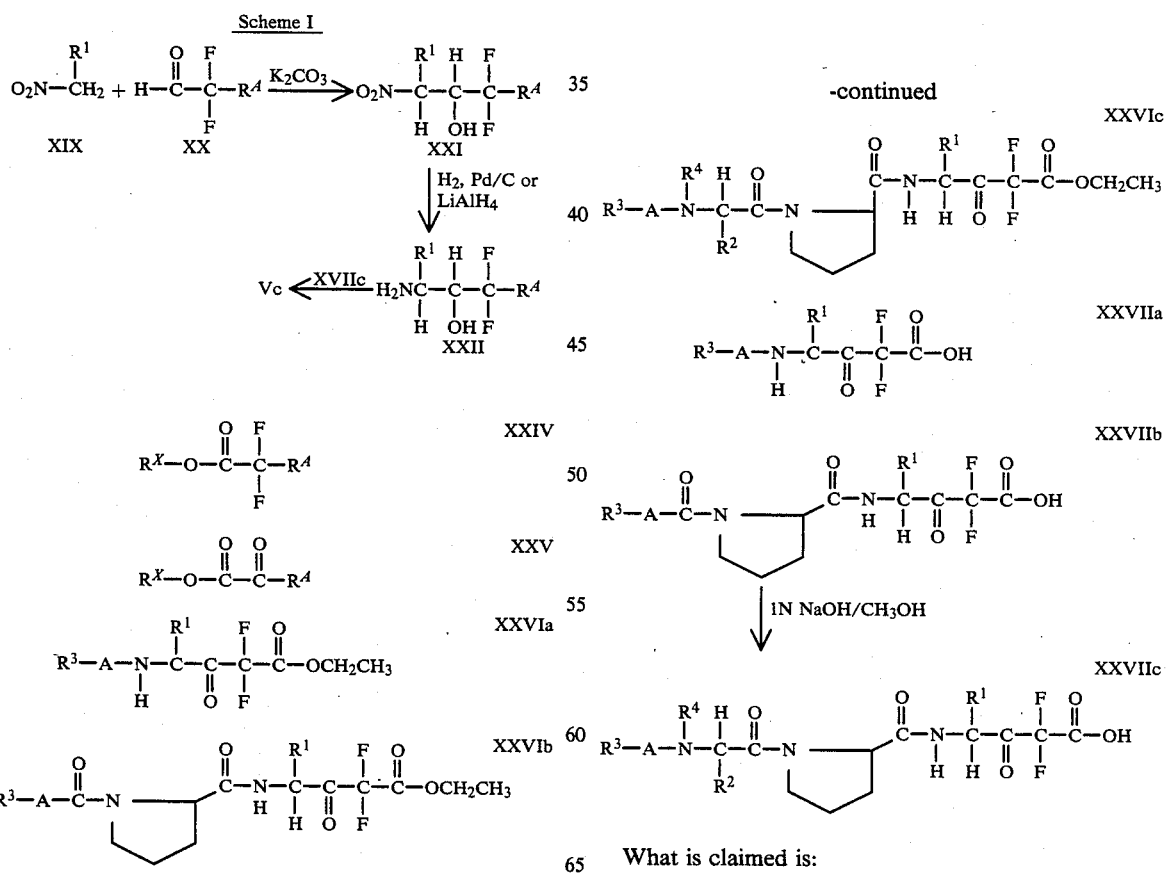
What is claimed is:
1. A compound of formula Ic:

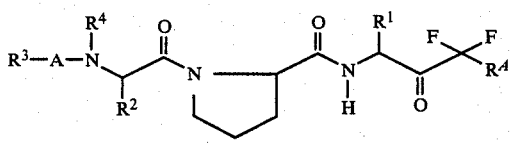

wherein
R$^1$ is an alkyl group containing from 1 to 5 carbons;
R$^2$ is an alkyl group containing from 1 to 10 carbons;
R$^3$ is an aryl group containing 6, 10 or 12 carbons substituted by acylsulfonamido containing an aryl of 6, 10 or 12 carbons which may be further substituted by a member selected from fluoro, chloro, bromo, iodo and nitro;
R$^4$ is selected from the group consisting of hydrogen and methyl;
A is selected from the group consisting of —CO—, —NHCO—, —OCO—, and —(SO$_2$)—;
R$^A$ is a group of formula II:

wherein X is NR$^C$, R$^C$ is hydrogen or CH$_3$; and
R$^B$ is selected from the group consisting of (6 or 10C)aryl(1-6C)alkyl, and pharmaceutically acceptable salts thereof.

2. A compound as claimed in claim 1 wherein
R$^1$ is an alkyl group containing 3 carbons;
R$^2$ is an alkyl group containing from 1 to 4 carbons;
R$^3$ is an aryl group containing 6 or 10 carbons substituted as described in claim 1;
R$^4$ is hydrogen; and
R$^C$ is hydrogen.

3. A compound as claimed in claim 2 wherein
R$^1$ is isopropyl;
R$^2$ is isopropyl;
R$^3$ is selected from a group consisting of 4-[[(phenylsulfonyl)amino]carbonyl]phenyl and 4-[[[(4-chlorophenyl)sulfonyl]amino]carbonyl]phenyl;
R$^4$ is hydrogen;
A is selected from a group consisting of —CO— and —OCO—;
R$^B$ is selected from a group consisting of phenylmethyl and 2-phenylethyl; and
R$^C$ is hydrogen.

4. A compound as claimed in claim 3 which is N-[4-[[[(4-chlorophenyl)sulfonyl]amino]carbonyl]benzoyl]-L-valyl-N-[3,3-difluoro-1-(1-methylethyl)-2,4-dioxo-4-[(2-phenylethyl)amino]butyl]-L-prolinamide, or a pharmaceutically acceptable salt thereof.

5. A compound as claimed in claim 3 which is N-[4-(phenylsulfonylaminocarbonyl)benzoyl]-L-valyl-N-[3,3-difluoro-1-(1-methylethyl)-2,4-dioxo-4-[(2-phenylethyl)amino]butyl]-L-prolinamide, or a pharmaceutically acceptable salt thereof.

6. A salt as claimed in claim 1 wherein said salt is made with a base forming a physiologically acceptable cation.

7. A pharmaceutical composition comprising a compound of claim 1 or a pharmaceutically acceptable base-addition salt thereof in an amount sufficient to inhibit human leukocytic elastase and a pharmaceutically acceptable diluent or carrier.

8. A composition as claimed in claim 7 wherein said composition is in the form of a liquid or powdered aerosol.

9. A method of treating emphysema in a living mammal comprising administering to the mammal a pharmacologically effective amount of a compound of claim 1.

* * * * *